United States Patent
Kolody et al.

(10) Patent No.: US 6,598,275 B1
(45) Date of Patent: Jul. 29, 2003

(54) LOW SHADOW RADIOLUCENT SURGICAL TABLE, CLAMP SYSTEMS, AND ACCESSORIES THEREFORE

(75) Inventors: Timothy Kolody, Lorain, OH (US); Ward L. Sanders, Albion, PA (US); Victor M. Selig, Euclid, OH (US); Joseph T. Sestak, Erie, PA (US); Yury Keselman, Beachwood, OH (US); Viroon Mai Ujjin, Montgomery, AL (US); John von Buelow, Oak Park, CA (US); Vijendra Nalwad, Thousand Oaks, CA (US); Richard C. Blanchard, West Hollywood, CA (US); Jonathan Scheiner, Upland, CA (US)

(73) Assignee: Steris, Inc., Temecula, CA (US)

( * ) Notice: Subject to any disclaimer, the term of this patent is extended or adjusted under 35 U.S.C. 154(b) by 112 days.

(21) Appl. No.: 09/804,361

(22) Filed: Mar. 12, 2001

(51) Int. Cl.[7] ............... A44B 21/00; A61G 13/10; B25B 5/04; F16B 1/00
(52) U.S. Cl. ............... 24/455; 24/457; 24/458; 24/525; 5/600; 5/601; 248/228.6; 248/229.26
(58) Field of Search ............... 24/525, 455, 457, 24/458, 563, 545, 555, 716; 604/322; 248/229.26, 228.6; 403/59; 5/600, 601, 621

(56) References Cited

U.S. PATENT DOCUMENTS

| 1,285,517 A | * | 11/1918 | White ............... 5/600 |
| 2,212,156 A | | 8/1940 | Erdley |
| 3,046,072 A | | 7/1962 | Douglass, Jr. et al. |
| 3,339,913 A | | 9/1967 | Anderson |
| 3,386,444 A | | 6/1968 | Brenner et al. |
| 3,504,386 A | * | 4/1970 | Rossi ............... 5/601 |
| D221,910 S | | 9/1971 | Brendgord |
| 3,981,492 A | | 9/1976 | Hallmann |
| 4,018,412 A | | 4/1977 | Kees, Jr. et al. |
| 4,033,539 A | * | 7/1977 | Bardocz ............... 248/228.6 |
| 4,069,813 A | | 1/1978 | Gilula |
| 4,122,587 A | | 10/1978 | Weiss et al. |
| 4,143,652 A | | 3/1979 | Meier et al. |
| 4,145,612 A | | 3/1979 | Cooper |
| 4,146,793 A | | 3/1979 | Bergstrom et al. |
| 4,221,371 A | | 9/1980 | Kuphal |
| 4,287,422 A | | 9/1981 | Kuphal et al. |
| 4,346,298 A | | 8/1982 | Dixit |
| 4,355,631 A | | 10/1982 | LeVahn |
| 4,487,523 A | | 12/1984 | Monroe |
| 4,547,092 A | | 10/1985 | Vetter et al. |
| D287,625 S | | 1/1987 | Brendgord et al. |
| 4,698,837 A | | 10/1987 | Van Steenburg |
| 4,796,846 A | | 1/1989 | Meier et al. |
| 4,805,202 A | | 2/1989 | Deucher et al. |

(List continued on next page.)

Primary Examiner—Victor Sakran
(74) Attorney, Agent, or Firm—Fay, Sharpe, Fagan, Minnich & McKee, LLP

(57) ABSTRACT

A radiolucent surgical table is provided with a patient support member and includes a low shadow accessory interface profile formed by a plurality of interconnected curved surfaces disposed along the outer edge of the patient support member for selective attachment of a range of medical accessory devices. A clamping apparatus secures associated accessories to the outer edge, which has a top recess and an essentially planar and non-vertical side surface slanting inwardly from top to bottom and terminating in a flared lower edge extending beyond the bottom of the patient support member. The clamping apparatus includes an upper jaw member which has a downwardly projecting lip formed to conformably engage a section of the top recess. A lower jaw member is also included and has a hook region formed to surroundingly engage a section of the flared lower edge. A means is provided for joining the upper and lower jaw members.

36 Claims, 26 Drawing Sheets

U.S. PATENT DOCUMENTS

| | | | |
|---|---|---|---|
| 4,901,964 A | 2/1990 | McConnell | |
| 4,936,836 A | 6/1990 | Weickgenannt | |
| 4,971,037 A | 11/1990 | Pelta | |
| 5,014,969 A | 5/1991 | Schaefer | |
| 5,029,826 A | 7/1991 | Schaefer | |
| 5,077,780 A | 12/1991 | Lee, Jr. | |
| 5,078,705 A | 1/1992 | Edwards et al. | |
| 5,090,044 A | 2/1992 | Kobayashi | |
| 5,097,132 A | 3/1992 | Plummer | |
| 5,099,550 A | * 3/1992 | Beane et al. | 24/458 |
| 5,279,603 A | 1/1994 | Everett et al. | |
| 5,287,575 A | 2/1994 | Allen et al. | |
| 5,337,760 A | 8/1994 | Nichols | |
| 5,400,772 A | 3/1995 | LeVahn et al. | |
| 5,440,857 A | * 8/1995 | Shanok et al. | 52/716.8 |
| 5,535,973 A | 7/1996 | Bailey et al. | |
| 5,538,215 A | 7/1996 | Hosey | |
| 5,586,830 A | 12/1996 | Schwieker | |
| 5,613,254 A | 3/1997 | Clayman et al. | |
| 5,701,991 A | 12/1997 | Helmetsie | |
| 5,771,513 A | 6/1998 | Kirchgeorg et al. | |
| D408,537 S | 4/1999 | Stickley et al. | |
| 5,983,426 A | 11/1999 | Vanek et al. | |
| 5,983,468 A | * 11/1999 | Evans, III et al. | 24/457 |
| 6,023,800 A | 2/2000 | Stickley | |
| 6,073,284 A | * 6/2000 | Borders | 5/600 |

* cited by examiner

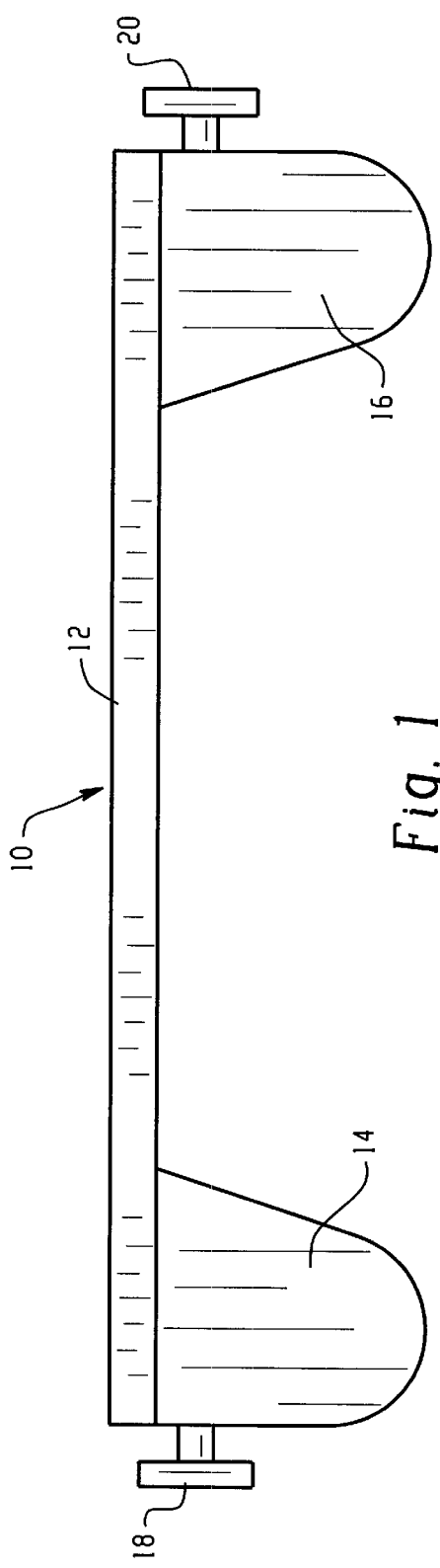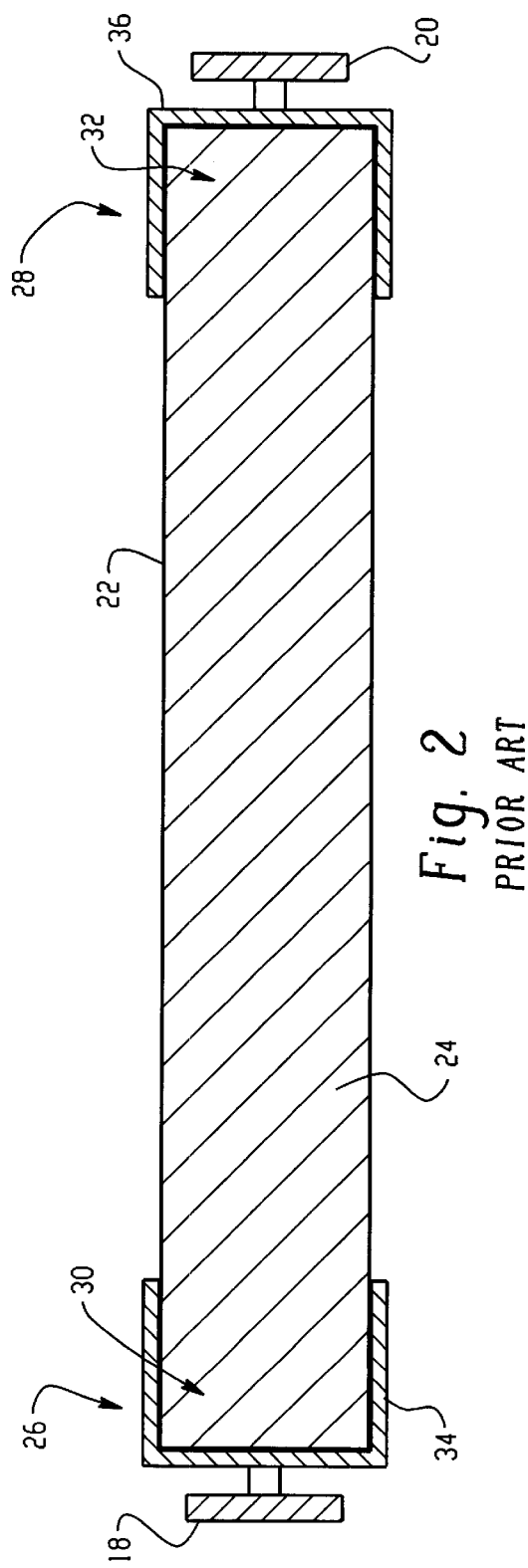

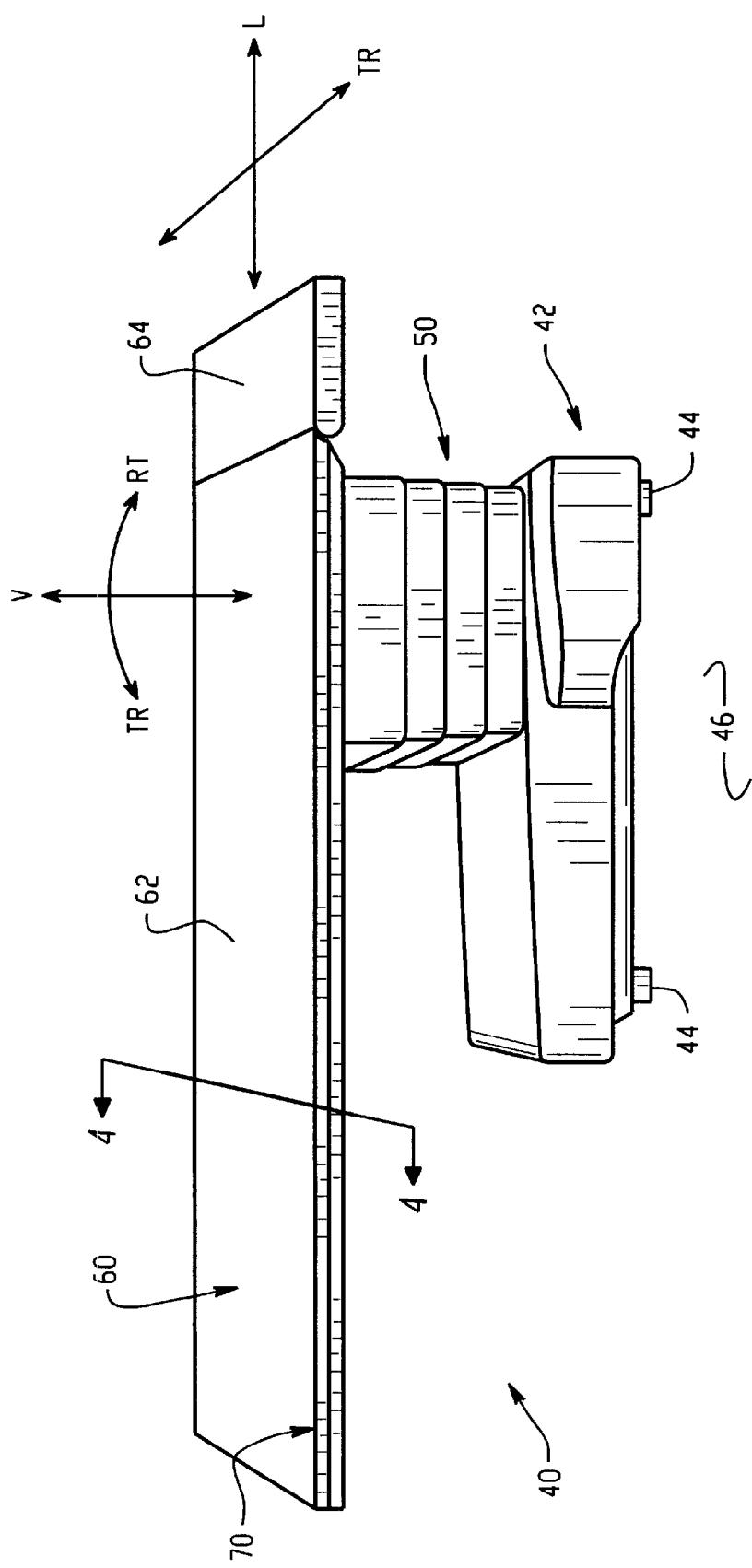

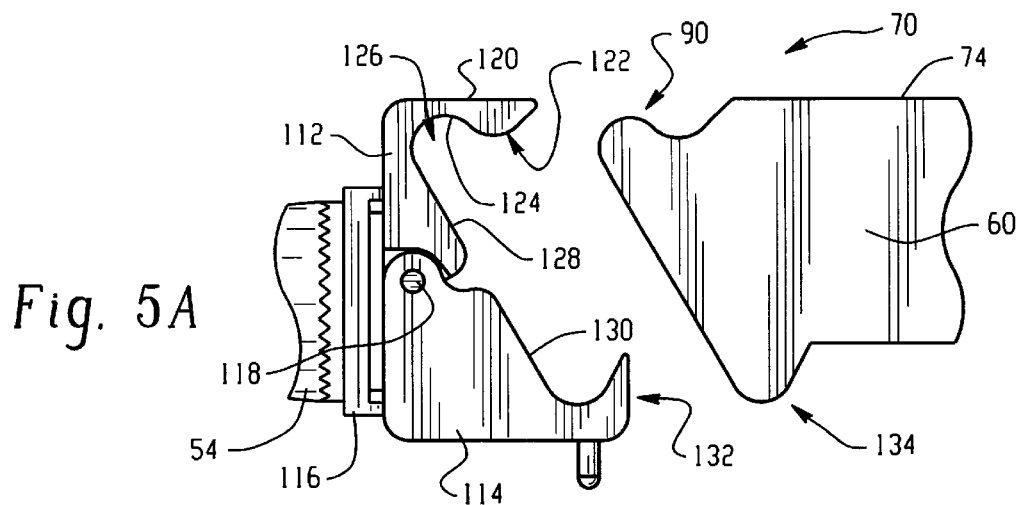
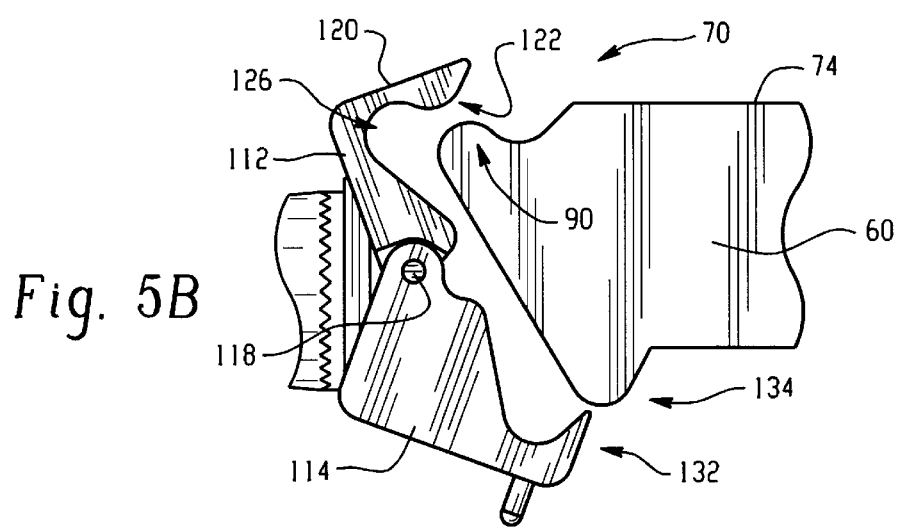
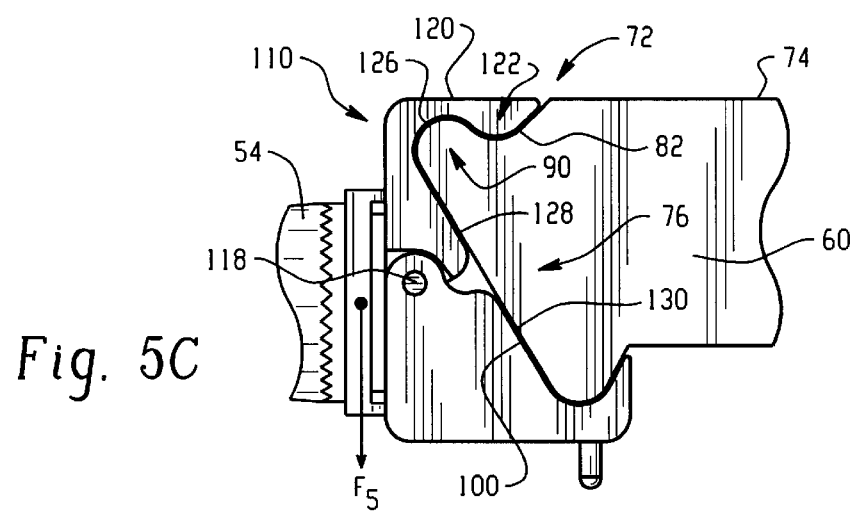

LOW SHADOW RADIOLUCENT SURGICAL TABLE, CLAMP SYSTEMS, AND ACCESSORIES THEREFORE

BACKGROUND OF THE INVENTION

1. Field of the Invention

The present invention relates to radiolucent surgical tables and, more particularly, to a radiolucent surgical table with a low radiographic shadow edge profile, a plurality of clamp systems for connection onto the edge profile, and a set of surgical accessories integrated with the clamps.

2. Description of the Prior Art

Conventional surgical tables include a flat patient support and a lower base for holding the patient support a predetermined distance from the floor. The base of conventional surgical tables commonly includes control apparatus for tilting the flat patient support through a range of orientations to facilitate performance of certain surgical procedures. Typical flat patient supports are made of surgical stainless steel and in most cases include a set of metal side rails supported along the edges of the table for holding surgical accessories, instrumentation, and the like. Typically, the side rails conform to an industry standard cross sectional size and configuration so that surgical accessories from any vendor source can be directly connected to surgical tables built by another vendor without modification of the attachment interface.

One disadvantage of stainless steel table tops of the type described above is that they block x-rays. Accordingly, their use in surgical or interventional procedures that require x-rays, fluoroscopic or other patient images to be taken are quite limited.

As a result, patient support tables have been proposed that utilize an x-ray translucent material, such as phenolic resins, in selected portions of the table top. The x-ray translucent material allows interoperative x-ray image signals to be generated using fluoroscopic devices, C-arm or CT scanners and other imaging equipment.

One such example of a prior art radiolucent table is shown at FIG. 1. As illustrated in cross section, the flat patient support 10 includes a substantially planar table top member 12 formed of a x-ray translucent material such as, for example, a carbon fiber material or a phenolic resin such as sold under the trade name SPAULDITE. Due mainly to load carrying capacity limitations and to enhance stiffness, the table top 12 is supported on either side by a pair of longitudinally extending metal frame members 14, 16. Each of the metal frame members 14, 16 are attached to the bottom surface of the table top member 12 using a suitable cement such as an epoxy, fasteners, or the like. A pair of side rail members 18, 20 are held in a fixed relationship relative to the metal frame members 14, 16 as illustrated. The side rail members 18, 20 have a size and shape that conform to the industry-wide standards noted above.

One disadvantage of the flat patient support 10 illustrated in FIG. 1 is that the metal frame members 14, 16 as well as the side rail members 18, 20 generate shadows when the patient support 10 is used in radiographic imaging procedures. As a result, only the portion of the radiopaque table top member 12 that is disposed between the pair of metal frame members 14, 16 is usable for radiographic imaging. This limitation becomes more pronounced when the table is tilted relative to the x-ray generator. The angle of the table relative to the x-ray source effectively shortens the distance between the metal side frame members 14, 16 as viewed from the x-ray source thus reducing the shadow-free areas in the radiographic image.

FIG. 2 illustrates another prior art surgical table configuration that is somewhat useful in radiographic imaging and in certain interventional procedures. As shown there, a predominant feature of the flat patient support 22 is a relatively thick slab 24 of radiographic material having a generally rectangular cross section. The slab 24 is provided on opposite transverse edges 26, 28 with a substantially square accessory interface profile 30, 32 as shown. Each of the accessory interface profiles 30, 32 are sized and shaped to receive a pair of accessory coupler members 34, 36 on the opposite transverse edges 26, 28 of the radiopaque slab 24. In turn, each coupler member 34, 36 carries an industry standard side rail member 18, 20 of the type described above. In that way, most commercially available accessories can be used with the table.

One drawback to the "slab" type radiolucent surgical tables shown in FIG. 2 is that the accessory coupler members 34, 36 are typically formed of metal and therefore obstruct x-ray signal propagation through portions of the table along the table edges. As a result, undesirable shadows are formed in the radiographic image.

Simple removal of the accessory coupler members 34 or 36 does not completely-solve the shadow problem. The vertical surfaces along the square edges of the accessory interface profiles 30, 32 lead to shadows in radiographic images. The shadows are caused because, during normal use of the table, the vertical edges of the profile are typically aligned in a substantially parallel relationship with x-ray signal propagation. As a result, the edge surfaces tend to attenuate the x-ray signal to a substantial degree greater than the flat horizontal surfaces and, accordingly, the vertical edge surfaces generate shadows in the radiographic image.

It is, therefore, desirable to provide a radiolucent surgical table that presents a substantially uniform attenuation characteristic to x-ray signals in both the lateral and transverse directions and with the table held flat or tilted relative to the x-ray signal source. In that way, the radiographic images of a patient disposed on such surgical table would be free and clear of extraneous shadows.

Copending application Ser. No. 09/804,287 filed on Mar. 12, 2001 and assigned to the assignee of the instant application provides such a table. In addition to being substantially x-ray shadow free overall, a surgical accessory interface profile is provided so that a wide range of surgical accessories can be easily and directly connected anywhere along the edge of the table top. The accessory interface profile presents a substantially uniform attenuation characteristic to x-rays passing through the table top and table top edges regardless of the angle of the table top relative to the x-ray source.

There is a need, therefore, for providing a set of clamp apparatus for connecting a plurality of medical accessories onto the interface profile of the radiolucent table. Preferably the clamp modalities are selected based on intended use with specific medical accessories and, in that way, the clamps provide the desired support for the medical accessories with which they are paired for ease of use, reduction in cost and to minimize size.

SUMMARY OF THE INVENTION

In accordance with the present invention, therefore, a shadow free radiolucent patient support table is provided including substantially planar top and bottom surfaces held apart in an opposed relationship. The radiolucent patient support table is preferably formed of an outer layer of carbon fibers surrounding an inner foam core. The outer longitudinal edges of the support table define a substantially continuous medical appliance support interface for selectively connecting a plurality of associated medical appliances to the table. The medical appliance support interface generally comprises a non-planar first connection area defined on the top surface of the surgical table and a second connection area defined on the side of the table top. The non-planar first connection area is shaped to provide first and second static supporting forces against an associated medical appliance, when connected to the table, in directions substantially parallel to and perpendicular with the top and bottom surfaces of the table. The second connection area is shaped to provide third and fourth static supporting forces against the associated medical appliance in third and fourth directions substantially parallel to and perpendicular with the top and bottom surfaces. The first and third forces cooperate to support a load moment generated by the medical accessory held by the table edge. The second and fourth forces cooperate to support the medical accessory against gravity and in a vertical direction.

In accordance with one aspect of the invention, the non-planar first connection area includes a curved lip surface extending along the upper edge of the table top and at least one recess defined between a pair of wall surfaces that converge at a bight region of the at least one recess. The lip and recess are preferably formed as a continuous smoothly curved surfaces disposed along the outer longitudinal edges of the table top.

In accordance with yet another aspect of the invention, the second connection area includes a substantially planar surface held at an oblique angle relative to the substantially planar top and bottom surfaces. The planar surface of the second connection area forms an acute angle with the top surface of the table and forms an obtuse angle with the bottom surface of the table. In that way, the second connection area generates a static counter-force against the associated medical appliance connector in a downward direction relative to the table top so that a downwardly directed lip formed on the connector is forced into tight engagement with the at least one recess defined by the first connection area.

In accordance with a still further aspect of the present invention, a segmented medical appliance connector is provided for attaching a wide range of surgical accessories directly to the table top at selected positions along the interface profile. The connector includes movable upper and lower jaws that are adapted to clamp onto the interface profile.

In accordance with still yet a further aspect of the invention, a unitary appliance connector is provided for attaching surgical accessories to the table top. The unitary connector includes a resilient engagement area that is adapted to be press-fitted onto the interface profile of the table top. The unitary connector has no moving parts and therefore is easy to use and can be sterilized conveniently.

In accordance with still yet a further aspect of the invention, a clamping apparatus for securing an associated accessory to an outer edge of an associated patient support member is disclosed. The outer edge of the patient support member has a top recess and an essentially planar and non-vertical side surface slanting inwardly from top to bottom and terminating in a flared lower edge extending beyond the bottom of the patient support member. The clamping apparatus includes an upper jaw member which has a downwardly projecting lip formed to essentially conformably engage a section of the top recess of the patient support member. A lower jaw member is also included and has a hook region formed to surroundingly engage a section of the flared lower edge of the patient support member. A means is provided for joining the upper and lower jaw members.

In one aspect of the clamping apparatus, the means for joining comprises a direct connection between the upper and lower jaw members whereby the upper jaw member, the lower jaw member, and the direct connection form a single unitary piece made from a resilient material. Preferably, the clamping apparatus further includes a spring which is at least partially embedded in the upper jaw member and essentially conforms with the lip area whereby an associated accessory may be supported in a flexible manner by the clamping apparatus. The spring may optionally extend outside the unitary piece in an upward direction to provide a flexible hook for attaching the associated accessory.

In another aspect of the clamping apparatus, the means for joining comprises a hinge region with a pivot axis about which the upper and lower jaw members may relatively pivot. The joining also includes a means for effectuating closure of the upper and lower jaw members whereby the clamping apparatus firmly clamps to a portion of the outer edge of the patient support member.

It is a primary object of the invention to provide a radiolucent surgical table that presents a substantially uniform attenuation characteristic over the entire surface area of the table top in both lateral and transverse table top directions with the table held flat or tilted relative to the x-ray source.

It is another object of the invention to provide such a table top that includes an accessory interface profile along the edge of the table top so that various surgical accessories, instruments, and the like can be quickly and easily attached to the radiolucent table as needed. The accessory interface edge profile presents a substantially uniform x-ray attenuation characteristic because it is formed without flat surfaces in alignment with the x-ray propagation direction. Essentially all of the surfaces of the interface edge profile are curved, rounded, or flat and disposed at oblique angles relative to the x-ray propagation direction.

It is another object of the invention to provide a radiolucent surgical table with a low shadow accessory interface profile that is convertible for use in a wide range of surgical and interventional procedures by providing a set of intermateable table top portions that are selectively arranged and fastened together into various configurations as needed. Preferably, the table top portions are connected using simple pin type attachment mechanisms.

It is yet another object of the invention to provide medical appliance connectors that are adapted to cooperate with the interface profile defined in the surgical table top to support various surgical devices and instruments relative to the table.

These and other objects and benefits of the present invention will be described below.

BRIEF DESCRIPTION OF THE DRAWINGS

The invention may take physical form in certain parts and arrangements of parts, the preferred embodiments of which will be described in detail in this specification and illustrated in the accompanying drawings which form a part hereof, and wherein:

FIG. 1 is a cross-sectional view of a prior art radiolucent surgical table taken along a line (not, shown) extending in a direction transverse to the table;

FIG. 2 is a cross-sectional view of a prior art radiolucent surgical table taken along a line (not shown) extending in a direction transverse to the surgical table;

FIG. 3 is an isometric view showing the subject radiographic surgical table in accordance with a first preferred embodiment supported on a mobile base;

FIGS. 5A–5C illustrate a sequence of steps for connecting a generic segmented medical accessory connector onto the radiolucent table top;

FIG. 7c is a side view in partial phantom of the lamp system of FIG. 7a;

FIG. 8b is an exploded isometric view of the spring clamp system of FIG. 8a;

FIG. 8c is a cross-sectional view of the spring clamp system of FIG. 8a;

FIG. 9b is an exploded isometric view of the spring clamp system of FIG. 9a;

FIG. 9c is a cross-sectional view of the spring clamp system of FIG. 9a;

FIG. 10b is an exploded isometric view of the dual jaw direct clamp system of FIG. 10a;

FIG. 10c is a cross-sectional view of the dual jaw direct clamp system of FIG. 10a;

FIG. 11b is an exploded isometric view of the dual jaw indirect clamp system of FIG. 11a;

FIG. 11c is a cross-sectional view of the dual jaw indirect clamp system of FIG. 11a;

FIG. 12b is an exploded isometric view of the dual jaw indirect clamp system of FIG. 12a;

FIG. 13b is an isometric view of the pivot pin clamp system of FIG. 13a.

DETAILED DESCRIPTION OF THE PREFERRED EMBODIMENTS

Figure 4:
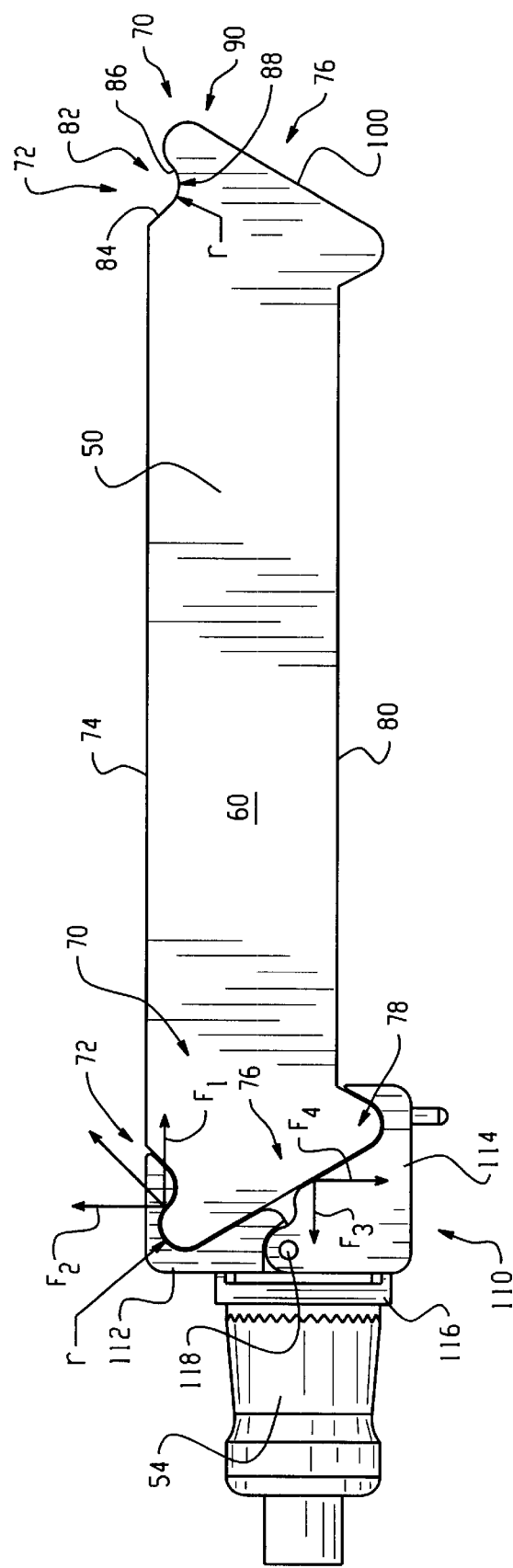
FIG. 4 is a cross-sectional view taken generally on line 4—4 of FIG. 3 and showing a segmented medical accessory attached thereto.

Referring now to the drawings wherein the showings are for the purposes of illustrating the preferred embodiments of the invention only and not for purposes of limiting same, FIG. 3 illustrates a floor mounted surgical table 40 with a radiolucent patient support member 60 and medical appliance support interface 70 formed in accordance with a first preferred embodiment of the invention. The table 40 has a somewhat conventional base section including a base member 42 which is supported by four legs 44, one leg 44 disposed at each corner of base member 42. The legs 44 may be of the retractable type which can be withdrawn into the base member 42 to permit wheels (not shown) to contact floor 46 and enable hospital personnel to conveniently reposition the surgical table 40 within a room. A vertical support and positioning column 50 is secured on a first lower end to the base member 42. The second or upper end of the column 50 supports the substantially planar radiolucent patient support member 60 in selected positions relative to the base member 42. The column 50 preferably includes control mechanisms and operators well known in the art for tilting the control housing together with the radiolucent patient support member 60 into various orientations relative to the base member 42 to facilitate performance of a wide variety of surgical, interventional, and imaging procedures. A basic raise and lower function is provided within the column 50 to enable the patient support member 60 to be moved vertically relative to the base member 42 as shown in FIG. 3 at arrow V. Additionally, a tilt function is provided within the column to enable the patient support member 60 to be pivoted relative to the base member 42. In that way, the support member 60 can be moved into Trendelenburg positions as shown in FIG. 3 at arrow T and reverse-Trendelenburg positions as shown at arrow RT.

Still further, the upper end of the column 50 preferably includes a X-Y translation mechanism (not shown) for enabling sliding movement between the radiolucent patient support member 60 and the column 50. A basic rail and bearing system of the type commonly used in industrial applications is preferably used. Systems of this type are available to provide smooth, accurate, and repeatable positioning between the respective members throughout the range of translation movement. In the present invention, longitudinal translation of the patient support member 60 in the direction L is provided relative to the column 50 over a range of travel of about twenty-four inches (24"). Transverse translation of the patient support member 60 in the direction TR relative to the column 50 is provided over a range of travel of about twelve inches (12"). Although x-y translation of the table 60 relative to the column 50 is preferred, in an alternative embodiment, the table is immovable relative to the column.

As shown in FIG. 3, the radiolucent, patient support member 60 of the first preferred embodiment is essentially formed as a monolithic single slab construction including a major body and leg support section 62 connected to the column 50 and a smaller headrest section 64 pivotally attached with the body and leg support section. 62.

Preferably, the headrest section 64 is selectively lockable in positions throughout a range of pivotal motion relative to the main body section 62. This allows the patient's head to be supported in raised or lowered positions as desired.

With continued reference to FIG. 3, the longitudinal edges of the radiolucent patient support member 60 form a medical appliance support interface 70 for selective connection of associated appliances to the table 40.

Preferably, the support interface 70 is formed to extend continuously around each outer longitudinal edge of the support member 60 including the body and leg support section 62 and the headrest section 64 as shown best in FIG. 3. A noted above, the support interface 70 adapts the outer edge of the surgical table 40 to selectively receive a wide variety of associated surgical accessory devices. Thus, by providing the support interface 70 along the outer edges, of the table top in a manner as shown in FIG. 3, the associated surgical appliances can be conveniently located anywhere along the sides of the surgical table 40 including positions on either side of a patient and adjacent the head of the patient.

With continued reference to FIG. 3, and with additional reference to FIG. 4, the subject medical appliance support interface. 70 includes a non-planar first connection area 72 defined on the top surface 74 of the radiolucent patient support member 60. In addition, the support interface 70 includes a second connection area 76 that is defined on the outer edge of the radiolucent patient support member 60 in a manner as shown. A non-planar third connection area 78 is defined at the bottom outer edge of the patient support member 60. The first 72 and second 76 connection areas support an associated medical appliance 54 relative to the table against gravity and normal downward loading. The second 76 and third 78 connection areas support the medical appliance relative to the table against upward loading such as may be experienced when the appliance is a medical restraint or the like.

FIG. 4 shows, in cross section, the preferred shape of the subject accessory interface 70 and the manner in which the interface is used to selectively connect various associated medical appliances 54 to the patient support member 60 through the use of novel clamp systems. With particular reference now to that figure, the non-planar first connection area 72 is shaped to provide a first support force $F_1$ against an associated medical appliance 54 in a first direction substantially parallel to the top, and bottom surfaces 74, 80 of the patient support member 60. Further, the first connection area 72 is shaped to provide a second supporting force $F_2$ against the associated medical appliance 54 in a second direction substantially perpendicular to the top and bottom surfaces 74, 80, respectively.

The second connection area 76 is defined generally on the edge of the patient support member 60 as shown to provide a third supporting force $F_3$ against the associated medical appliance 54 in a third direction substantially parallel to the top and bottom surfaces 74, 80 of the support member. The second connection area 76 is formed to also provide a fourth supporting force $F_4$ against the associated medical appliance 54 in a fourth direction substantially perpendicular to the top and bottom surfaces 74, 80.

As can be seen from the figure, the first and second connection areas 72, 76 cooperate to support the medical appliance relative to the table against gravity and normal downward loading. The static forces $F_1$–$F_4$ combine to provide the necessary resultant forces to support the associated medical appliance. The third connection area 78 is necessary only when upward loading is expected to be encountered.

Preferably, and in accordance with the present invention, the first connection area 72 includes at least one recess 82 defined between a pair of concave wall surfaces 84, 86 that converge at bight area 88 as shown. Essentially, the bight area 88 is formed in the valley between the pair of opposed concave wall surfaces 84, 86. Preferably, the bight area 88 is a continuous rounded surface formed between the opposed concave wall surfaces 84, 86 as shown. This configuration enables x-ray signals to pass through the first connection area 72 of the support interface 70 along a transmission path substantially perpendicular to the top and bottom surfaces 74, 80 without encountering surfaces parallel with the transmission path. Surfaces parallel with the transmission path as well as surfaces that are close to parallel with the transmission path absorb the x-ray signal to a larger degree than surfaces which are oblique or perpendicular to the x-ray path. Accordingly, by forming the first connection area 72 without surfaces parallel or close to parallel with the x-ray transmission path, the first connection area 72 enables a substantially shadow-free image along the outer edge of the radiolucent patient support member 60.

It is to be appreciated that the bight area 88 could include a flat surface between the opposed concave wall surfaces 84, 86 and parallel with the top and bottom surfaces 74, 80 of the support member 60 without adversely affecting x-ray signal propagation through the first connection area 72. This enables an elongated first connection area if desired. In that case, the upward supporting force $F_2$ would be spread out over a larger (wider as viewed in the figure) surface area.

The outer wall surface 86 is somewhat shorter than the inner wall surface 84 relative to the top surface 74 of the radiolucent patient support member 60 so that various medical accessories can be attached to the support member without extending above the plane defined by the top surface 74. In that way, the upper portion of the medical accessory connector essentially forms a planar extension of the table top surface 74. Alternatively, the outer wall surface 86 can be formed to be the same size as or larger than the inner wall surface 84 relative to the top surface 74 of the patient support member 60. In those equivalent structures, the upper portion of the associated medical accessory connector would extend above the plane defined by the top surface 74 when the connector is disposed in the clamped-on position relative to the support interface 70.

With continued reference to FIG. 4, the outer wall surface 84 extends outwardly relative to the center of the patient support member to form a downwardly curved lip area 90 as shown. Preferably, in accordance with the present invention, the curved lip area 90 as well as the recess 82 are substantially circular in cross section and are curved to define a first radius r. The curved lip area as well as the recess are preferably formed without interruption or breaks along the entire outer longitudinal edges of the radiolucent patient support member 60 as best shown in FIG. 3.

As is apparent from the cross sectional view of the patient support member 60 shown in FIG. 4, the first connection area 72 provides a convenient surface for hanging medical devices and other equipment on the edge of the surgical table. In order to provide precise mechanical locating of the associated medical devices relative to the table top, the second connection area 76 is formed to define a substantially planar locating surface 100 that is preferably disposed at an angle oblique to the top and bottom surfaces 74, 80 of the support member 60. Preferably, the locating surface 100 forms an angle of approximately 50 degrees relative to the top surface 74. In this configuration, the locating surface 100 provides an undercut in the patient support member 60 that is advantageously used to multiply the load moment generated by the associated medical accessory into a clamping force between the recess and curved lip area 82, 90 and a downwardly directed portion of a connector assembly fashioned to engage the recess and curved lip area.

In that regard and with attention now directed to the left portion of the cross sectional view shown in FIG. 4, a segmented medical accessory connector 110 is illustrated in tight mechanical engagement with the medical appliance support interface 70. As shown, the segmented connector 110 includes movable upper and lower jaw members 112, 114 that are carried on a main body portion 116 of the accessory connector. Preferably, in accordance with the present invention, the jaw members 112, 114 are pivotally connected to the main body portion 116 at a pivot joint 118. In that way, the jaws can be opened so that the accessory connector can be selectively attached onto the medical appliance support interface 70.

FIGS. 5A–5C illustrate the preferred manner in which the segmented medical accessory connector 110 is attached to the medical appliance support interface 70. Turning now to those figures, the medical accessory connector 110 is first brought in general relative alignment with the medical appliance support interface 70 as shown best in FIG. 5A. It is to be noted that preferably, the movable upper jaw member 112 includes a substantially planar top surface 120 that forms, in the connected position, an extension to the radiolucent patient support member 60 substantially within the plane of the top surface 74 thereof. Further, the movable upper jaw member 112 includes a downwardly projecting lip 122 and a curved concave surface 124 that defines a pocket 126 adapted to receive the curved lip area 90 of the support interface 70. Lastly, the movable upper jaw member 112 includes a substantially planar upper engagement surface 128 that is coextensive with a lower engagement surface 130 defined by the lower jaw member 114 when the accessory connector 110 is disposed in a closed orientation as shown in FIG. 5A.

Turning now to FIG. 5B, the subject segmented medical accessory connector 110 is shown in its opened position whereat the upper and lower jaw members 112, 114 are rotated relative to the pivot connection 118 into the positions shown for ready attachment onto the medical appliance support interface 70. The upper jaw member 112 is pivoted upwardly to an extent to enable the downwardly projecting lip 122 to pass freely over the curved lip area 90 of the support interface 70. In a similar fashion, the lower movable jaw member 114 is pivoted downwardly to an extent to enable a hook region 132 of the lower jaw member to pass freely over a flared edge 134 of the third connection area 78 of the radiolucent patient support member 60. Preferably, in accordance with the present invention, the movable upper and lower jaw members are biased into the closed position illustrated in FIGS. 5A and 5C and are brought into the opened orientation for ready attachment onto the support interface when the jaws are simultaneously held open by mechanical means such as by manual manipulation.

FIG. 5C illustrates the segmented medical accessory connector 110 in its operative closed position and clamped onto the patient support member 60 via the appliance support interface in accordance with the present invention. As shown, the movable upper jaw member 112 is securely seated against the first and second connection areas 72, 76. The movable lower jaw member 114 is similarly securely seated against the second and third connection areas 76, 78. In that regard, the downwardly projecting lip 122 of the upper jaw member 112 is held in place within the recess 82 of the support interface 70 through engagement with the concave wall surfaces 84, 86. Further, the pocket 126 formed on the underside of the upper jaw member 112 is securely held in place through mechanical engagement with the curved outer surface of the lip area 90 formed on the outer edge of the patient support member 60. The upper and lower engagement surfaces 128, 130 are brought into planar engagement with the locating surface 100 formed as an undercut on the patient support member 60. In that way, a downward force $F_5$ generated by the associated medical appliance 54 attached to the accessory 110 generates a torque moment centered about the curved lip area 90. The force of the torque moment is converted by the planar interface between the locating surface 100 and the upper and lower engagement areas 128, 130 into a downward force that is utilized to ensure snug engagement between the downwardly projecting lip 122 and pocket 126 of the upper jaw member 112 against the lip area and recess 90, 80 of the support interface.

Figure 6A:
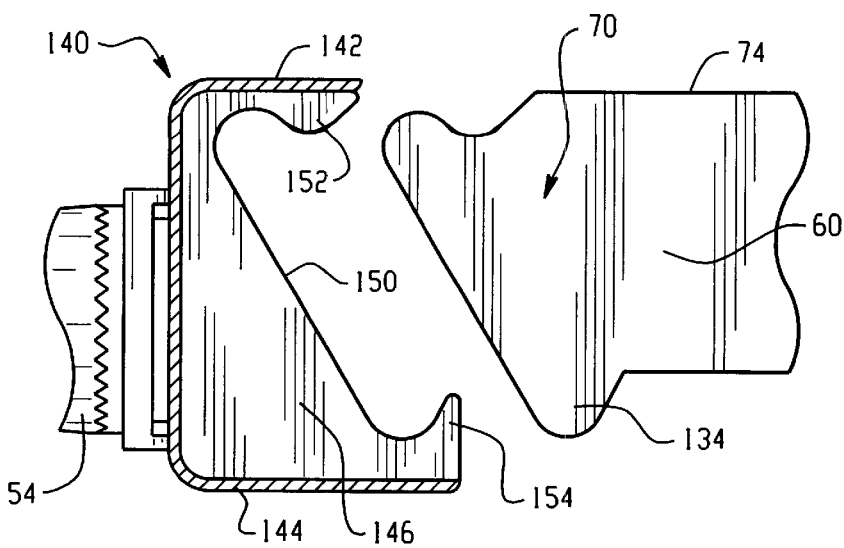
FIGS. 6A–6C show a sequence of steps for connecting a unitary medical appliance connector onto the subject radiolucent table top.
Figure 6B:
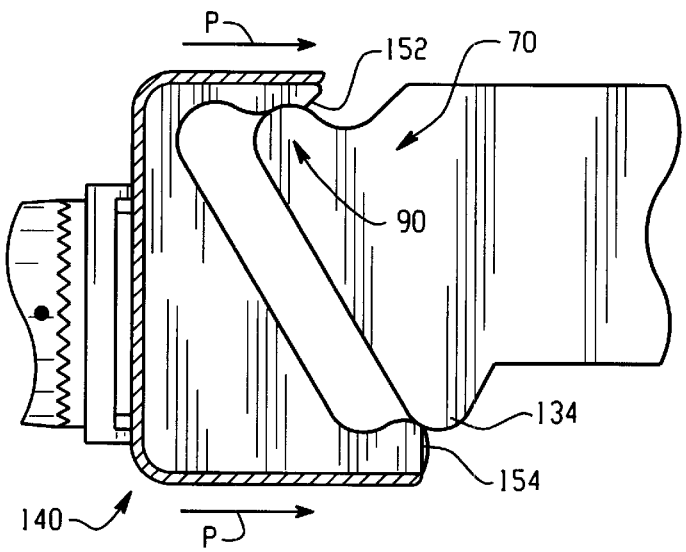
Figure 6C:
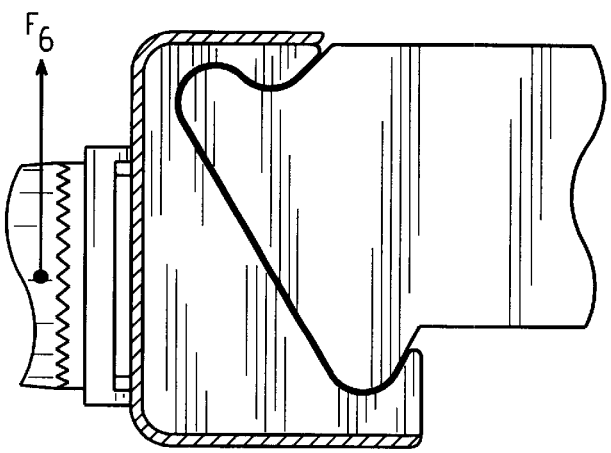

FIGS. 6A–6C illustrate the subject medical appliance support interface 70 used in conjunction with a substantially unitary medical accessory connector 140 that can provide both upward and downward forces against the interface. As shown first in FIG. 6A, the connector 140 is illustrated in operative position adjacent the support interface whereat a substantially planar top surface 142 of the accessory connector is brought into relative alignment with the top surface 74 of the support member 60. Preferably, the top surface 142 is formed by the upper portion of an outer C-shaped frame member 144 that is adapted to carry a resilient deformable holding element 146 as shown. Preferably, as illustrated, the holding element 146 has an outer surface 150 that is shaped as the mirror image of the outer surface of the medical appliance support interface 70. In that way, the unitary medical accessory connector 140 can be brought into intermated connection with the support interface 70 by simply pushing the accessory connector 140 onto the interface 70 against the force of the resilient deformable holding element 146 and into the position illustrated in FIG. 6C.

FIG. 6B illustrates the unitary medical accessory connector 140 midway between fully detached and attached positions. As illustrated, a downwardly projecting lip member 152 is compressed by the lip area 90 of the support interface 70. Similarly, the lower hook region 154 of the deformable holding element 146 is compressed by the lower flared edge 134 of the support interface 70. The unitary medical accessory connector 140 is brought into the final connected position illustrated in FIG. 6C by moving the connector relative to the patient support member 60 in the direction marked P in FIG. 6B. The unitary connector is snap-fitted into place simply by using a force adequate to overcome the friction and compressive force on the resilient deformable holding element 146. Preferably, the holding element 146 is formed of any suitable resilient elastomeric material such as a stiff rubber material or the like.

Figure 7B:
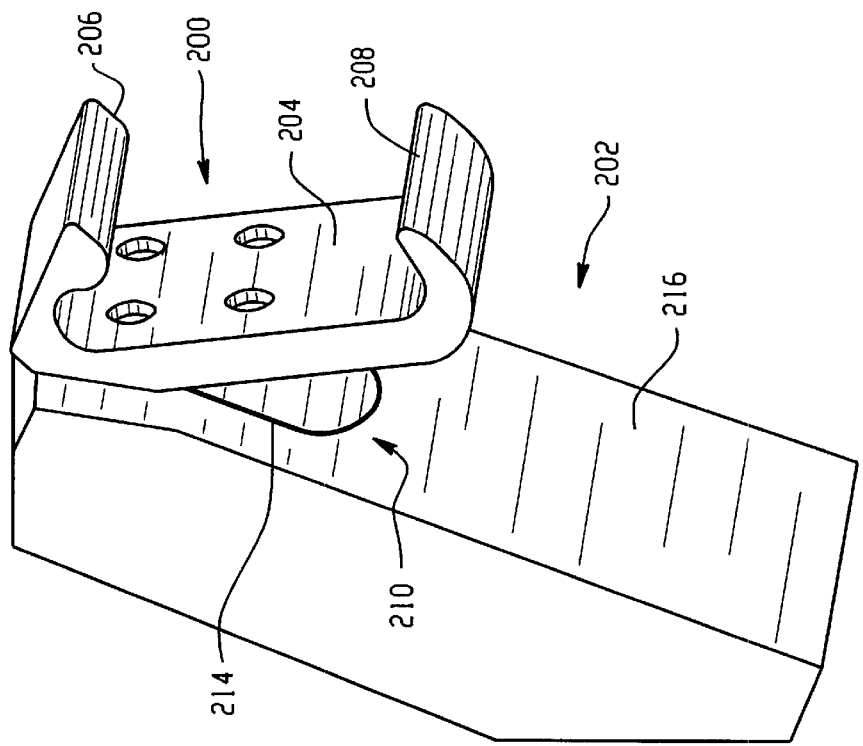
FIG. 7b is an isometric view of the resilient lamp system of FIG. 7a from a different viewing angle.
Figure 7A:
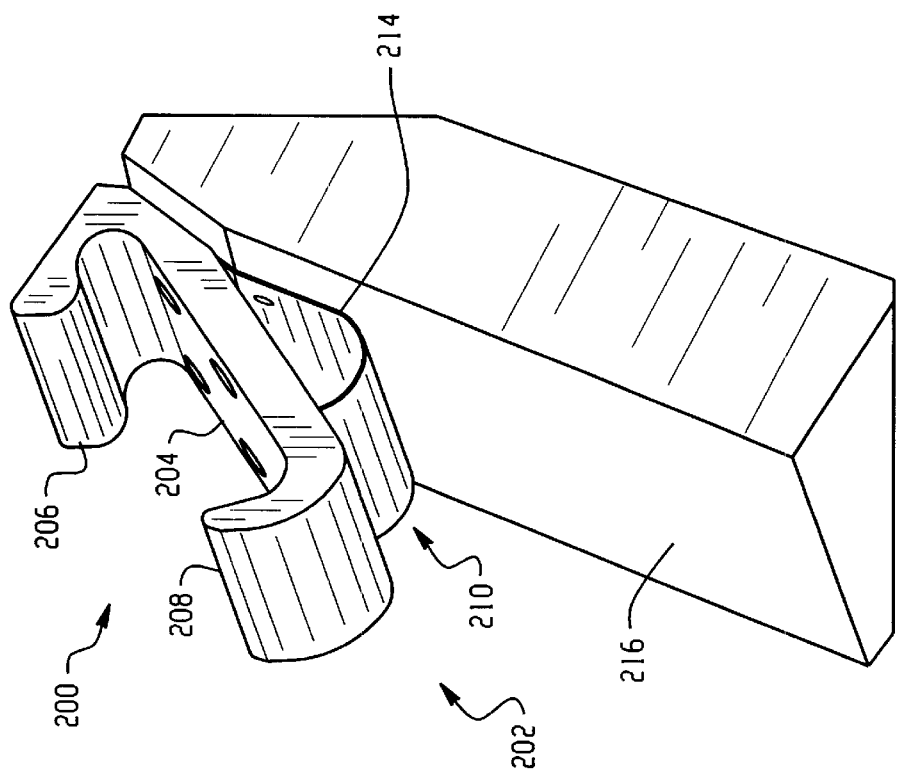
FIG. 7a is an isometric view showing a resilient lamp system in a table-controlled pendant support accessory according to a first embodiment of the invention.
Figure 7C:
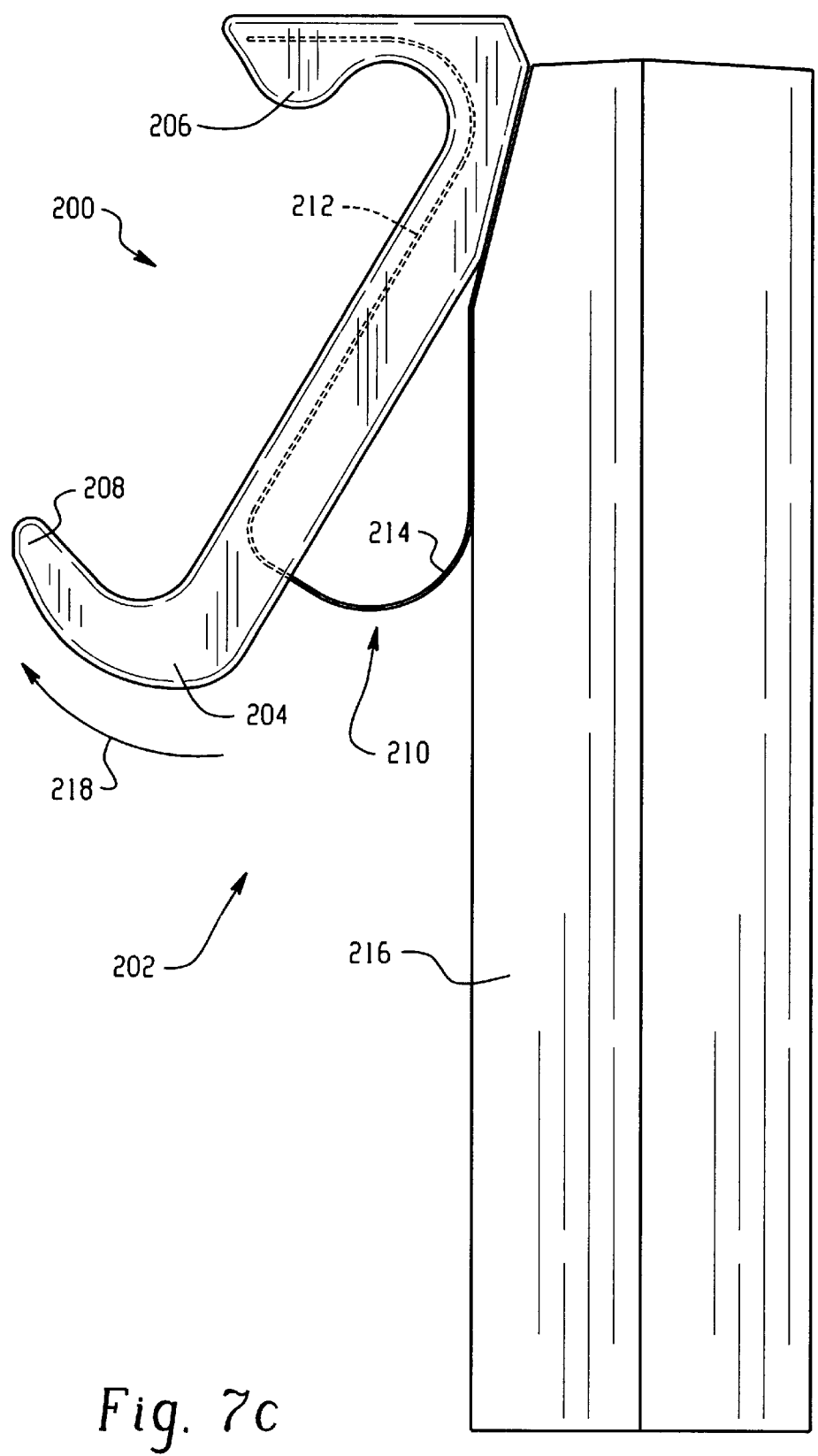

Similar to the above discussion in connection with the segmented medical accessory connector 110, the unitary connector 140 illustrated in FIGS. 6A–6C includes a lower hook region 154 that is adapted to surroundingly engage the flared edge 134 of the third connection area 78 disposed at the lower outer edge of the support member 60. The engagement between the hook region and the flared edge helps prevent detachment of the unitary medical accessory connector 140 from the support interface 70 when the medical appliance 54 attached thereto is subjected to an upward oriented disrupting force $F_6$. FIGS. 7a, 7b, and 7c illustrate a resilient clamp system 200 in a table control pendant support accessory 202 in accordance with a first preferred embodiment of the invention. As illustrated there, the resilient clamp system 200 includes a generally C-shaped resilient rubber member 204 defining an upper lip area 206 and a lower catch area or hook 208. Preferably, the C-shaped rubber member 204 is formed from any suitable sterilizable resilient material such as, for example, rubberized polymers.

A generally S-shaped spring clip 210 includes a first portion 212 embedded within the rubber member 204 and a second portion 214 extending therefrom in an upward direction substantially as shown. It is to be appreciated that the shape of the first portion 212 of the spring clip 210 generally conforms to the contours of the upper lip area 206 of the rubber member 204. In that way, substantial loads can be supported by the accessory 202. The second portion 214 of the spring clip 210, however, extends outwardly and upwardly from the central portion of the rubber member 204. In that way, the second portion 214 of the spring clip adapts the resilient clamp system 200 for connection with a wide range of devices such as, for example, an associated table control pendant 216 as shown. It is to be appreciated that the second portion 214 of the spring clip 210 can take on any size, shape, or configuration so that the resilient clamp system 200 can be used in combination with a wide range of surgical table accessories.

In the embodiment illustrated, the resilient nature of the spring clip 210 permits the associated table control pendant 216 to move slightly relative to the associated radiographic surgical table as needed. This is useful to prevent damage to the table control pendant such as may be caused during inadvertent bumping or other contact with the pendant. The spring clip 210 provides a mechanical cushion between the control pendant and the table. In the past, control pendant support accessories were generally rigid in construction. Table control pendants were often shattered or cracked as a result of incidental or unintended contact.

In addition to the above, it is to be appreciated that the lower catch area 208 of the rubber member 204 is substantially more resilient (less stiff) than the upper lip area 206 owing to the arrangement of the first portion 212 of the spring clip 210 within the rubber member. This enable easy attachment of the resilient clamp system 200 onto the accessory interface of the associated radiographic surgical table. The upper lip area 206 is first positioned in place followed by a simple downward rotation of the rubber member through an arc 218 until the resilient clamp system 210 pops over the lower lip area of the table and into place on the table interface edge.

Figure 8A:
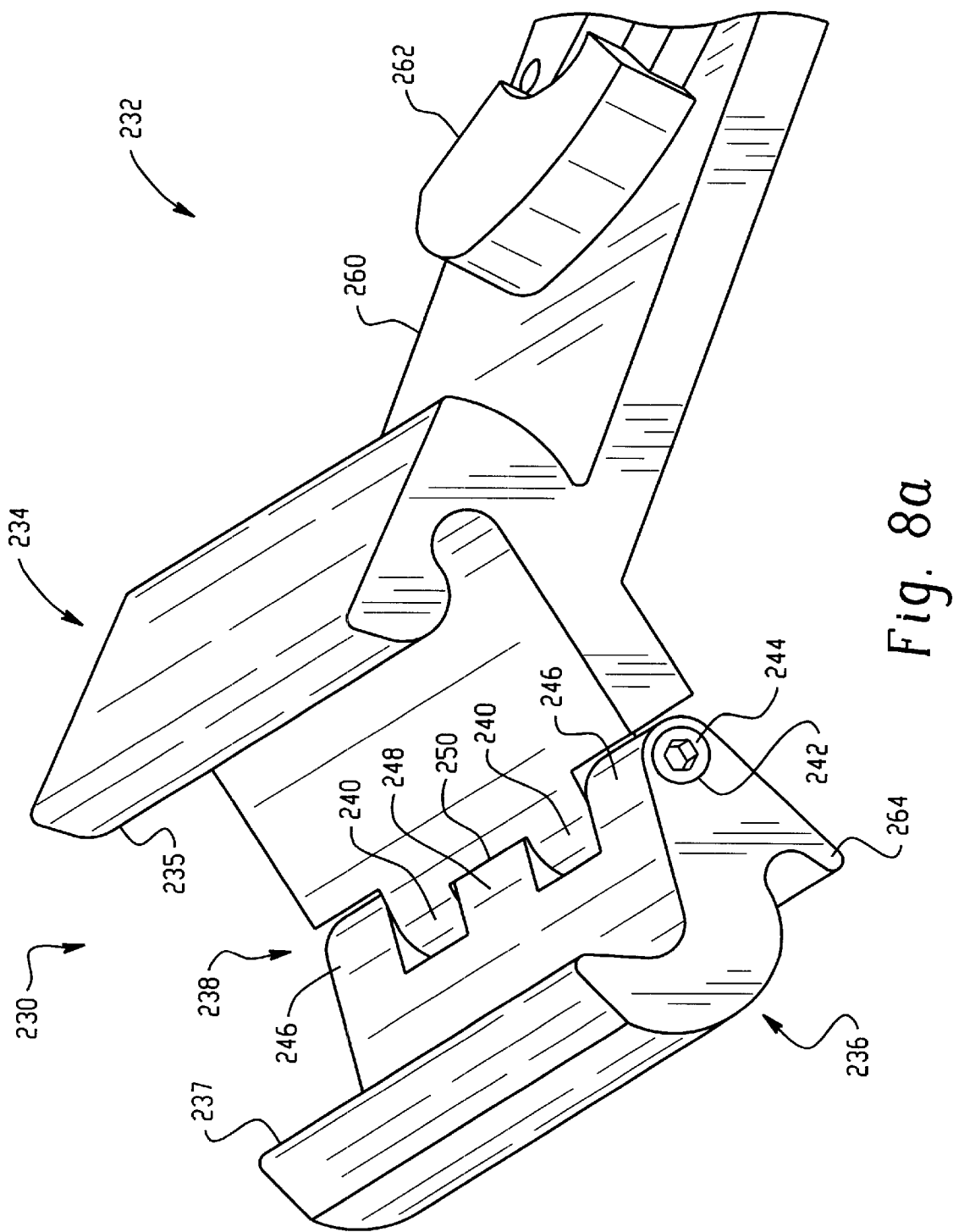
FIG. 8a is an isometric view showing a spring lamp system in an arm board accessory according to a second embodiment of the invention.
Figure 86:
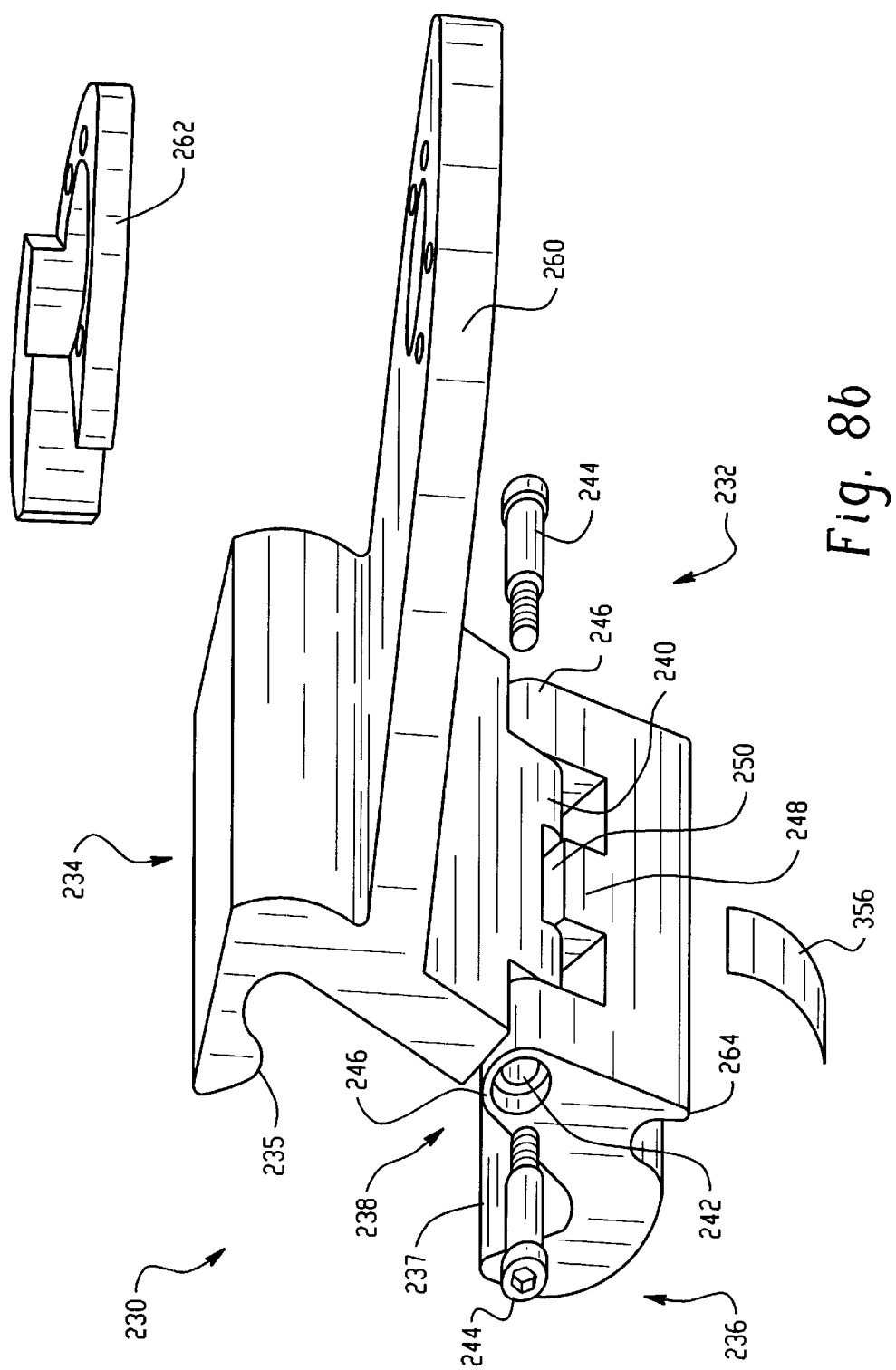
Figure 8C:
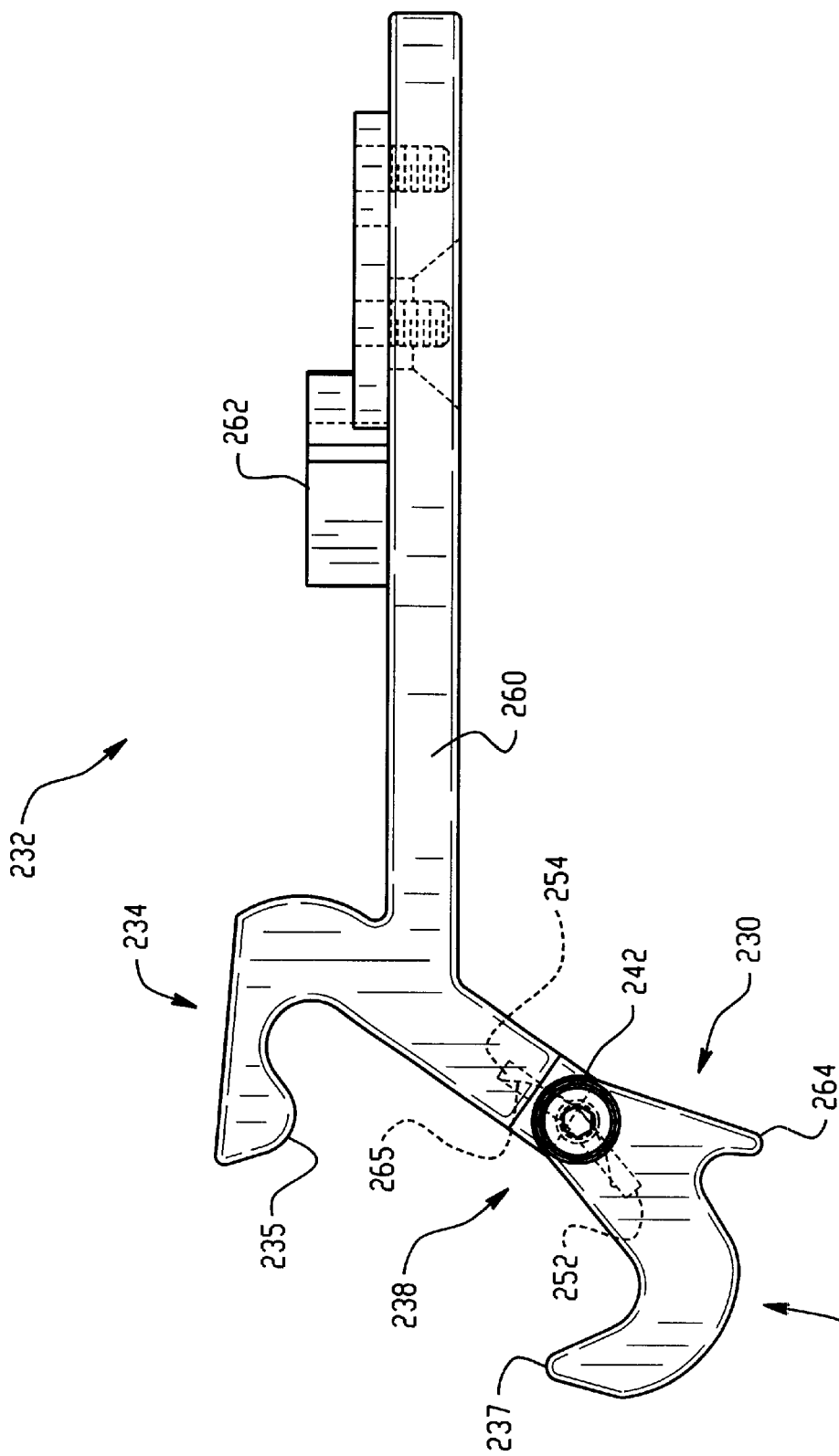

FIGS. 8a, 8b and 8c illustrate a spring clamp system 230 in an arm board accessory 232 in accordance with a second preferred embodiment of the invention. Turning now to those figures, the spring clamp system 230 includes an upper jaw member 234 which has a downwardly projecting lip 235 formed to conformably engage a section of the top recess or connection area 72 of the patient support member 60. Upper jaw member 234 is pivotally attached to a lower jaw member 236 which has a lower catch area or hook 237 formed to surroundingly engage a section of the flared lower edge 134 of the patient support member 60. Preferably, a hinge region 238 is formed at the connection interface between the upper and lower jaw members. In the embodiment illustrated, the upper jaw member 234 includes a pair of downwardly extending spaced apart hinge ears 240. The hinge ears are provided with threaded holes 242 to selectively receive a pair of opposed shoulder screws 244. The shoulder screws extend through suitable openings provided on a second pair of hinge ears 246 arranged on the lower jaw member 236 opposite from the upper hinge area 240. A central boss 248 extends upwardly from the lower jaw member 236 into the gap 250 formed between the hinge ears 240 on the upper jaw member 234. A first pocket 252 having a generally rectangular cross section is formed in the central boss 248 as shown best in FIG. 8c. A second pocket 254 is formed in the upper jaw member 234 in the gap 250 between the upper hinge ears 240. Preferably, the first and second pockets are identically formed and located in a face-to-face relationship to receive a leaf spring member 256 in the area defined by the pockets. The leaf spring member can be formed of any suitable material such as, for example, spring steel and is provided to bias the upper and lower jaw members 234, 236 in a closed position onto the accessory interface of the associated surgical table.

In the embodiment illustrated in FIGS. 8a, 8b, and 8c, it is to be appreciated that the upper jaw member 234 includes an outwardly extending generally planar shelf member 260 which is adapted to rotatably receive an associated armboard support platform 262. The armboard support platform 262 together with the shelf member 260 and spring clamp system 230 collectively form the armboard accessory 232 in accordance with the second preferred embodiment of the invention.

To facilitate removal of the spring clamp 230, a boss 264 is preferably molded into lower jaw member 236 whereby a manual force opposing and overcoming the clamping force generated by leaf spring member 256 may be applied to disengage lower jaw member 236 from third connection area 78 of the radiolucent patient support member 60. Absent the manual force, the spring clamp 230 holds the accessory 232 on the associated table against both upward and downward forces.

Figure 9A:
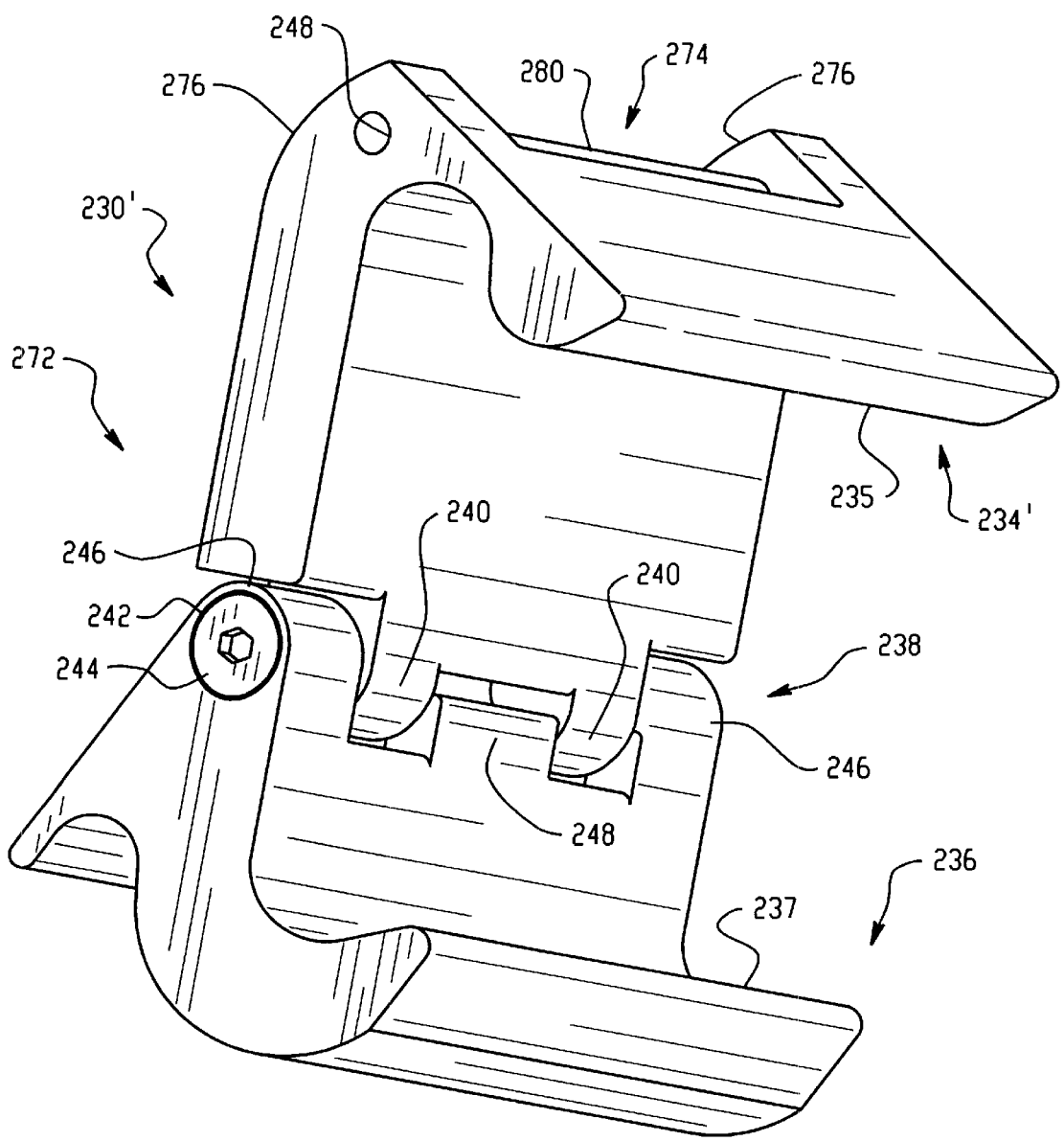
FIG. 9a is an isometric view showing the spring clamp system of FIG. 8a in a restraint strap accessory in accordance with a third embodiment of the invention.
Figure 9B:
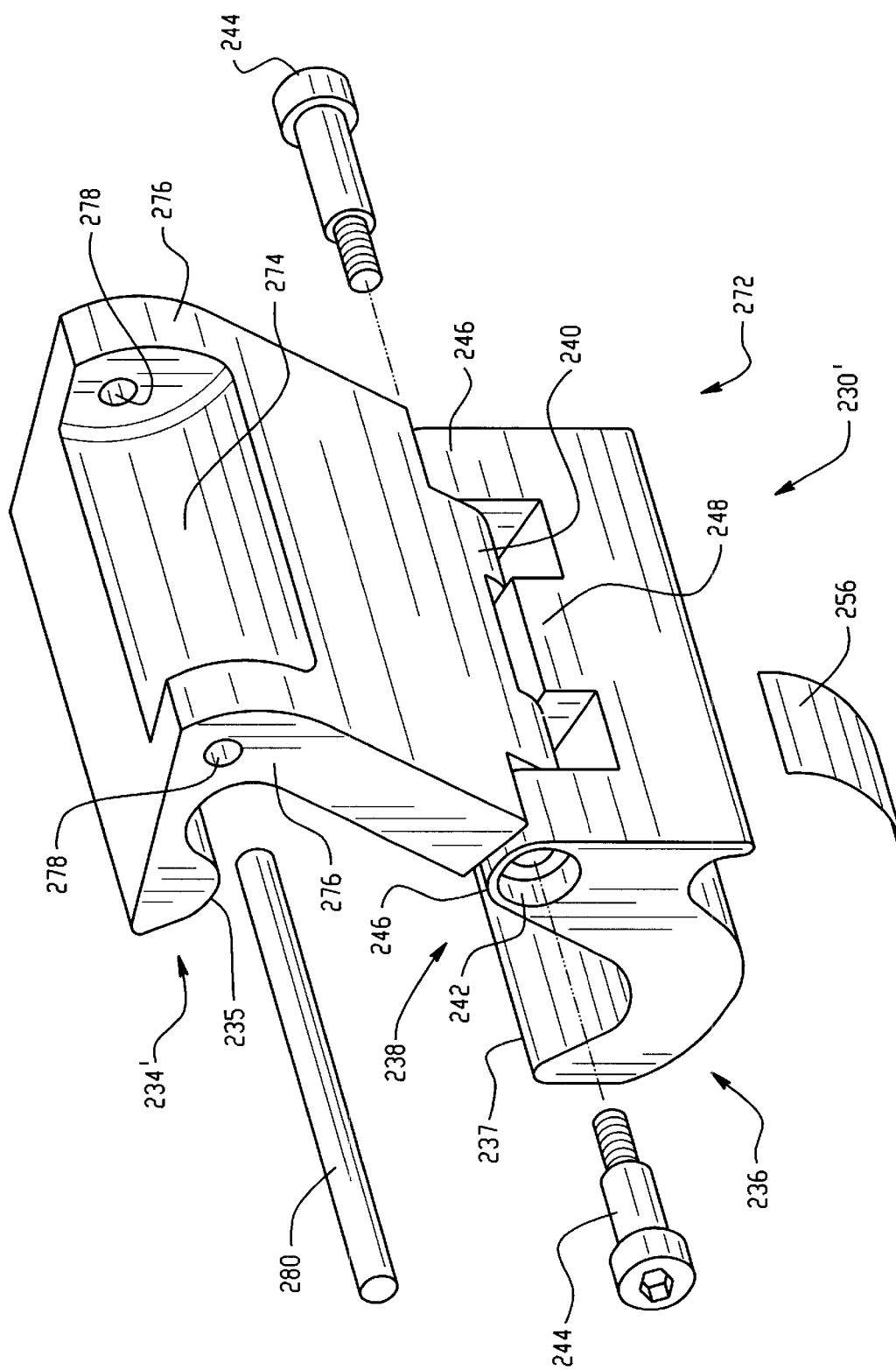
Figure 9C:
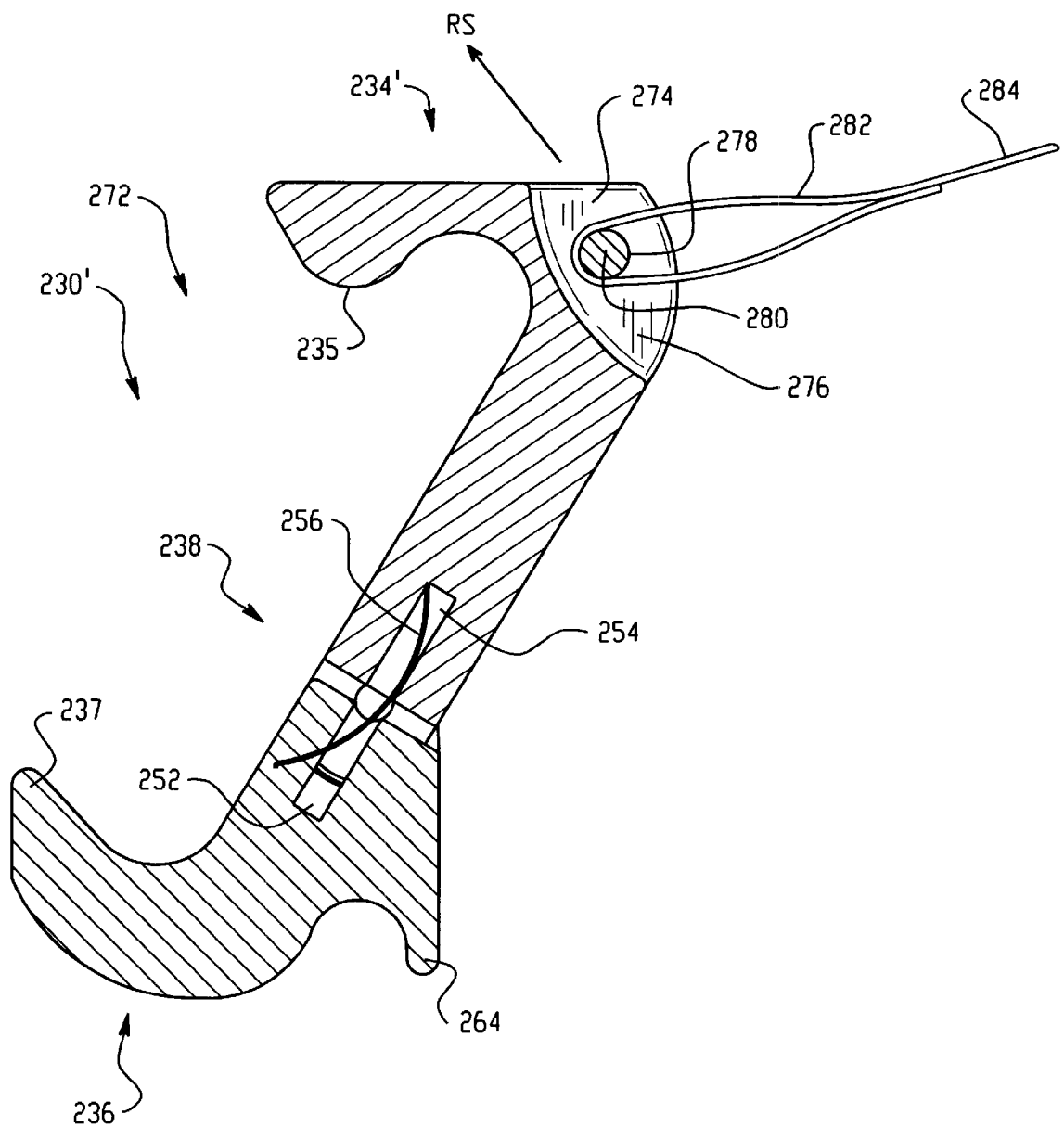

A third preferred embodiment of the invention is shown in FIGS. 9a, 9b and 9c. Turning now to those Figures, the spring clamp system 230 described above in connection with FIGS. 8a–c is provided in a restraint strap accessory 272. The working portions of the upper and lower jaw members 234', 236 are formed and operate in a manner substantially identical to the spring clamp system 230 described above in connection with the armboard accessory 232. However, in the restraint strap accessory, the upper jaw member 234' defines a curved recess area 274 formed between a pair of spaced apart outwardly extending connection ears 276. Each connection ear is provided with an attachment opening 278 which are mutually aligned to receive a connection pin 280. Preferably, the connection pin 280 is press-fitted into the attachment openings 278 and thereby extends between the connection ears 276 across the recess area 274. The connection pin 280 provides a suitable attachment point for the loop portion 282 of an associated restraint strap 284.

Typical use of the restraint strap accessory 272 includes a pair of spring clamp systems 230' clamped onto sides of patient support member 60 with a restraining strap starting at the first spring clamp system 230', passing across patient support member 60 and preferably also across a portion of an associated patient (not shown) thereby providing restraint, and terminating at a second spring clamp system 230' on the other side of the table. Under this arrangement, any force exerted on the strap accessory 272 by patient movement will be directed essentially upward in a direction indicated in FIG. 9c as RS.

Figure 10A:
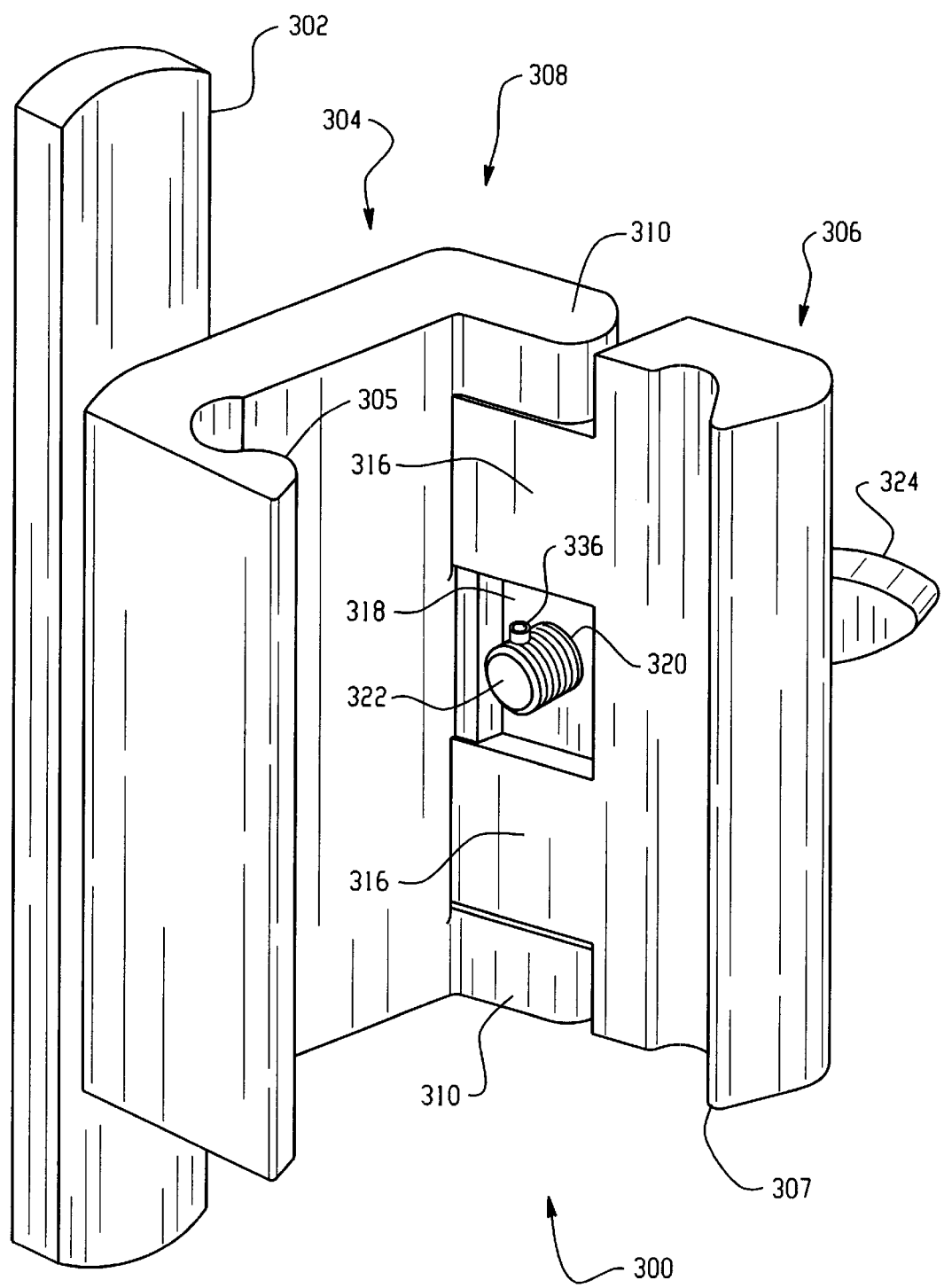
FIG. 10a is an isometric view showing a dual jaw direct clamp system in a rail adaptor accessory in accordance with a fourth embodiment of the invention.
Figure 10B:
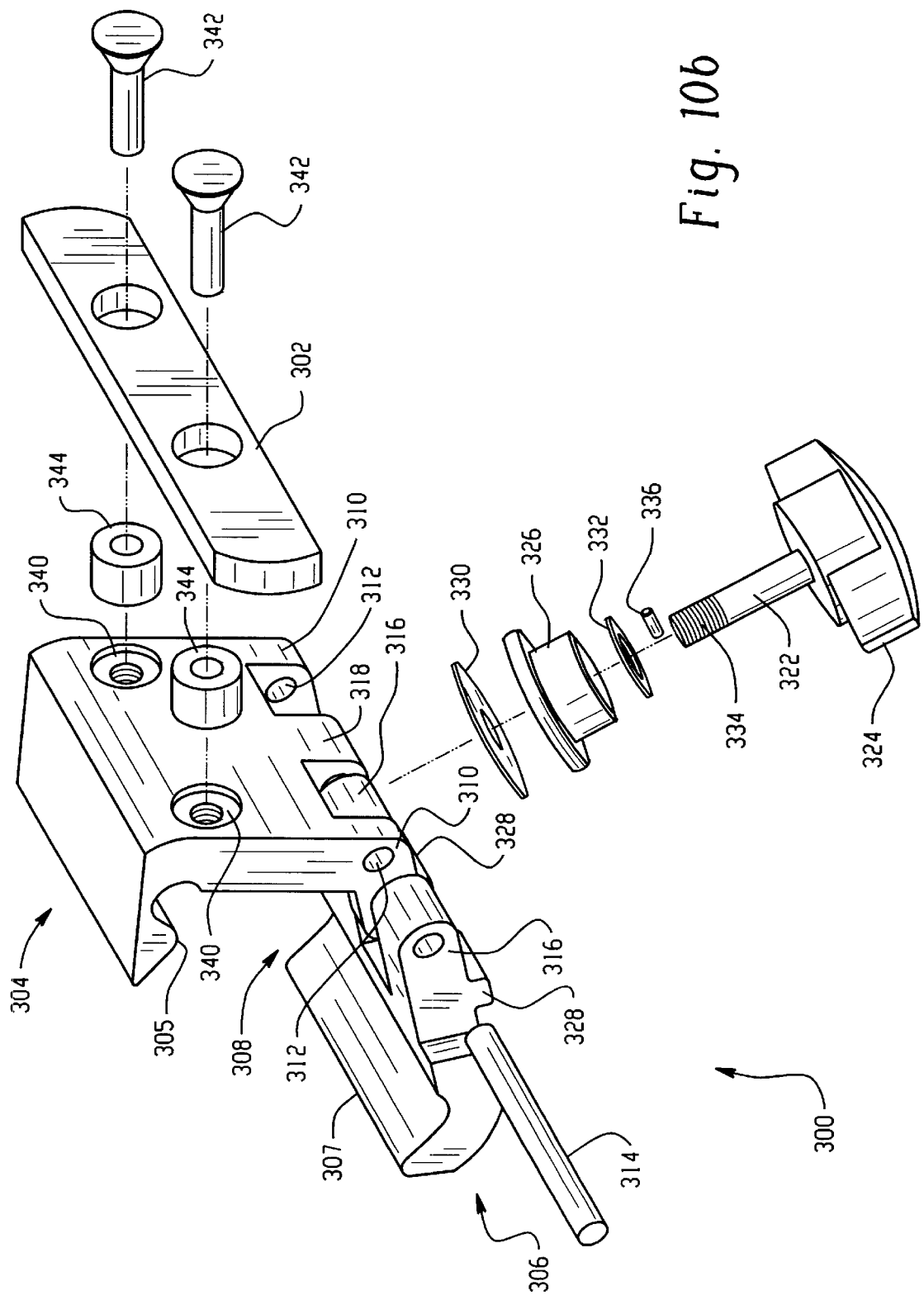
Figure 10C:
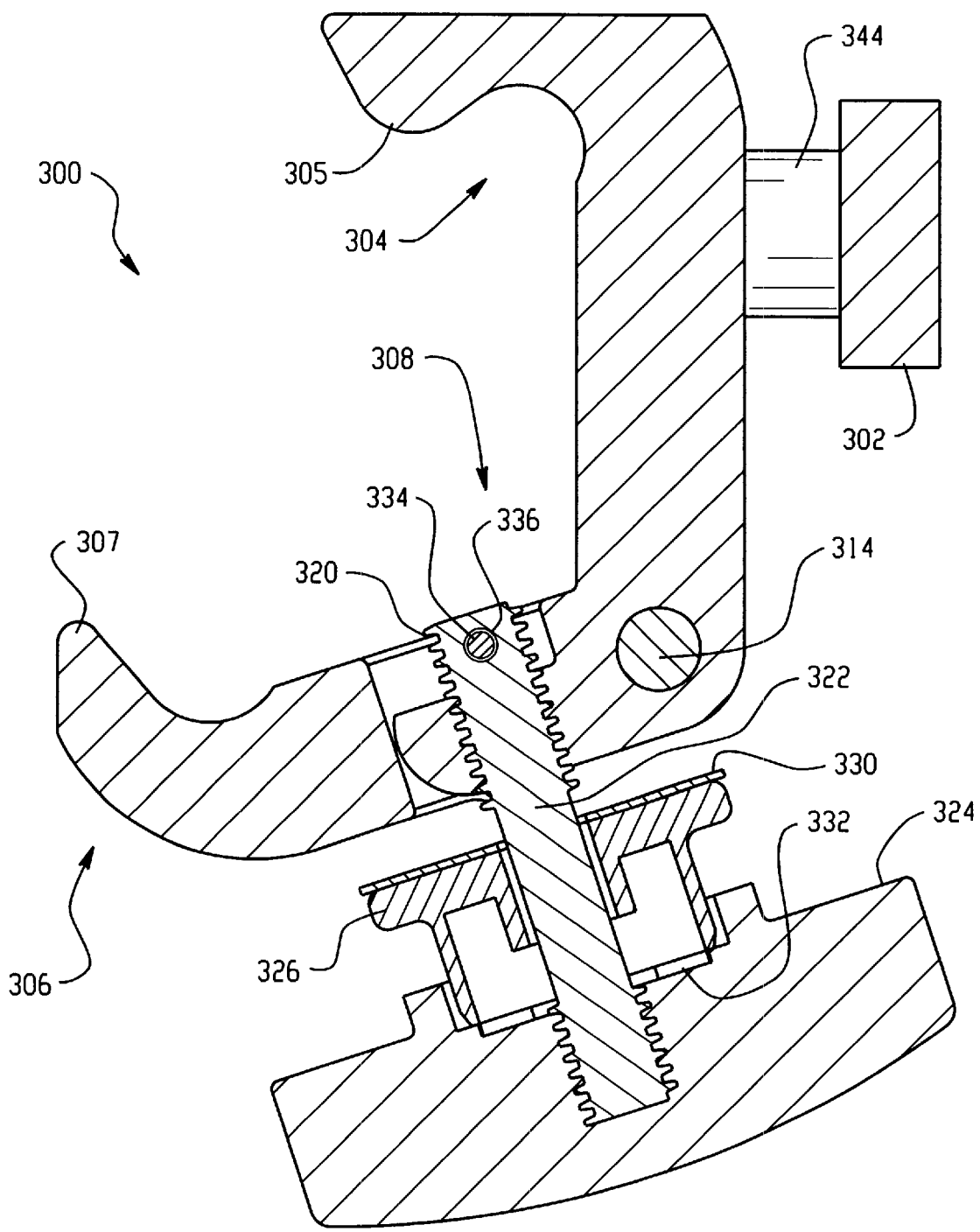

FIGS. 10a, 10b and 10c illustrate a dual jaw direct clamp system 300 for attachment of a rail adaptor accessory 302 in accordance with a fourth preferred embodiment of the invention. The dual jaw direct clamp system 300 includes an upper jaw member 304 which has a downwardly projecting lip 305 formed to conformably engage a section of the top recess or connection area 72 of the patient support member 60. Upper jaw member 304 is pivotally attached to a lower jaw member 306 which has a lower catch area or hook 307 formed to surroundingly engage a section of the flared lower edge 134 of the patient support member 60. Preferably, a hinge region 308 is formed at the connection interface between the upper and lower jaw members.

In the embodiment illustrated, the upper jaw member 304 includes a pair of spaced apart hinge ears 310. The hinge ears are provided with holes 312 to receive a dowel pin 314. Dowel pin 314 extends through suitable openings provided on a second pair of hinge ears 316 arranged on the lower jaw member 306 opposite from the upper hinge area 310. A central hinge ear 318 extends from the upper jaw member 304 into the gap 320 formed between the hinge ears 316 on the lower jaw member 306.

Central hinge ear 318 differs from hinge ears 310 at least in that it includes a threaded hole 320. A threaded stud 322 is received by a knob 324 and the threaded hole, 320 of third hinge ear 318. Rotation of threaded stud 322, obtained by manual rotation of knob 324, drives stud 322 inwardly whereby push button 326 is compressed against bosses 328 which extend essentially downward from hinge ears 316 of lower jaw member 306. The force of push button 326 against bosses 328 directs the lower jaw 306 about the pivot dowel pin 314 toward upper jaw 304 whereby a clamping action of the dual jaw direct clamping apparatus 300 to a portion of the outer edge of the patient support member 60 is effectuated.

Preferably, a large washer 330 is inserted over stud 322 between push button 326 and bosses 328, and small washer 332 is inserted over stud 322 between-push button 326 and knob 324. The washers provide improved mechanical action during clamp tightening. Large washer 330 is preferably a plastic washer, whereas small washer 332 is preferably a metal washer. It will be particularly noticed that the described mechanical action distributes the compressive force across an extended area of bosses 328. Stud 322 preferably has a hole 334 into which a retaining pin 336 is inserted to prevent stud 322 from being rotated fully out of the assembly.

So as to act as a rail mounting, upper jaw member 304 additionally has threaded holes 340 that receive screws 342. Screws 342 compressively hold rail standoffs 344 and rail 302 rigidly against upper jaw member 304 so that rigid mounting of rail 302 to patient support member 60 is effectuated by dual jaw direct clamp system 300. Of course, it is to be appreciated that at least two such clamps will usually be required to adequately support a rail of significant length, especially if the rail is in turn supporting additional items, as will usually be the case.

Figure 11A:
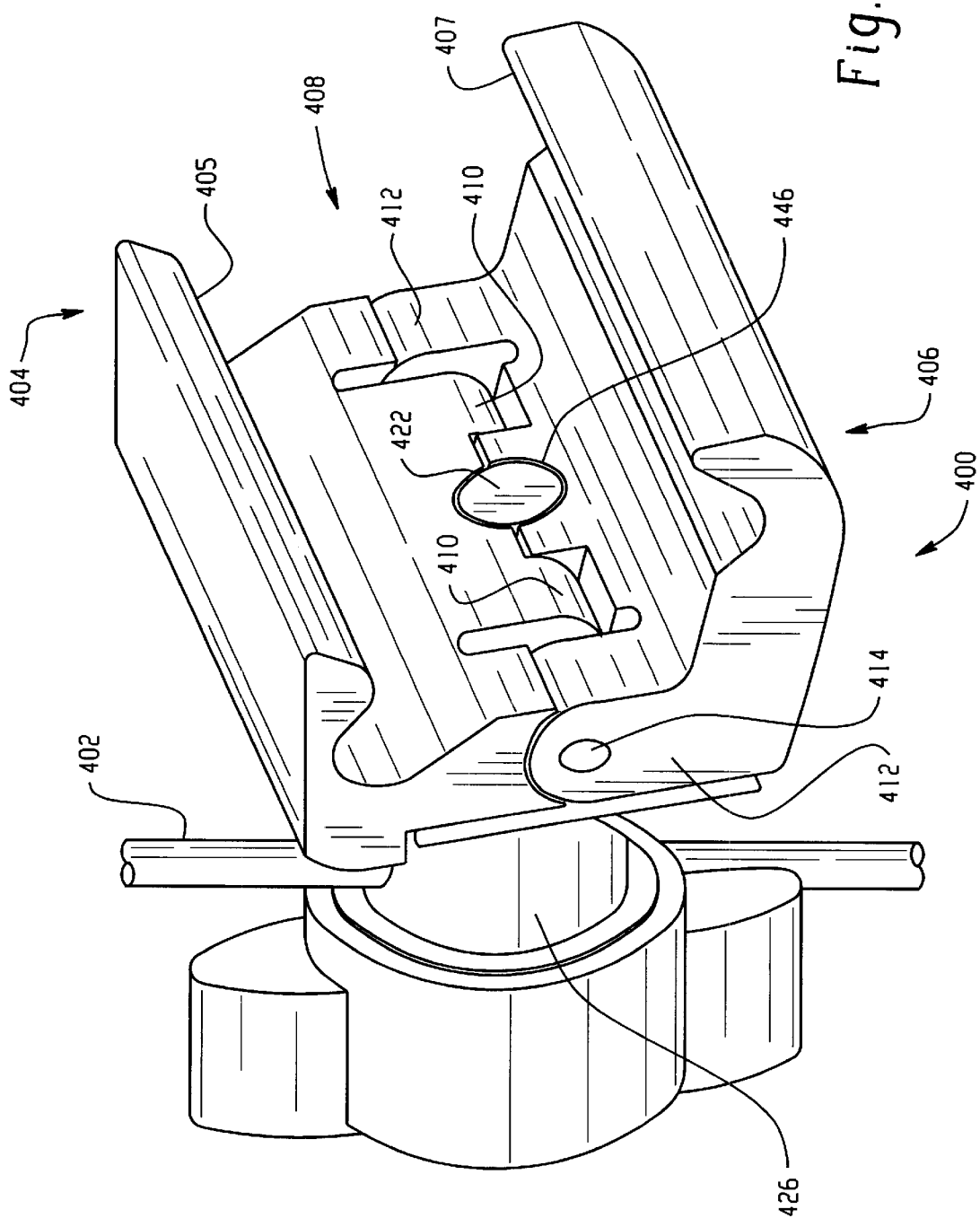
FIG. 11a is an isometric view showing a dual jaw indirect clamp system in a Clark socket accessory in accordance with a fifth embodiment of the invention.
Figure 11B:
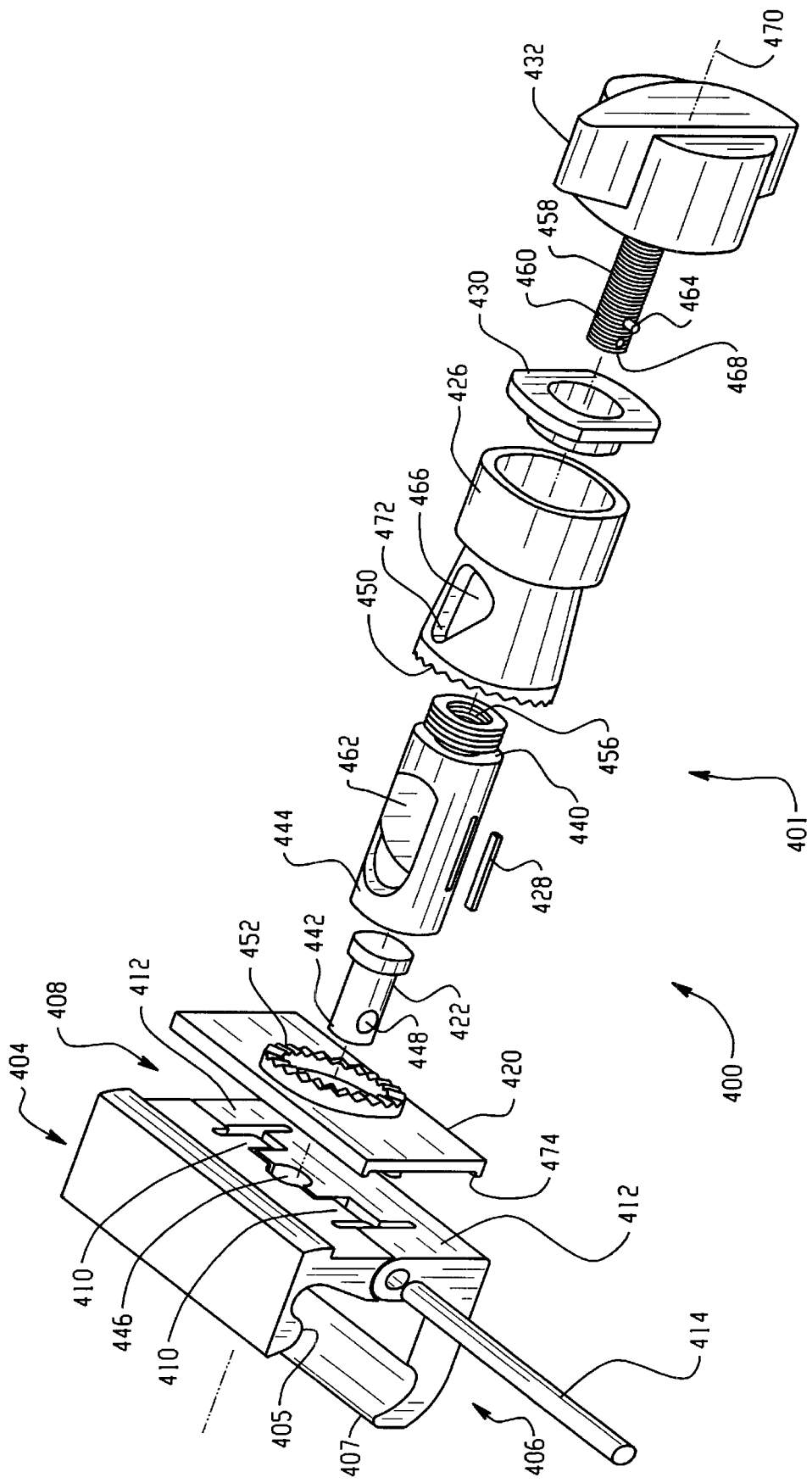
Figure 11C:
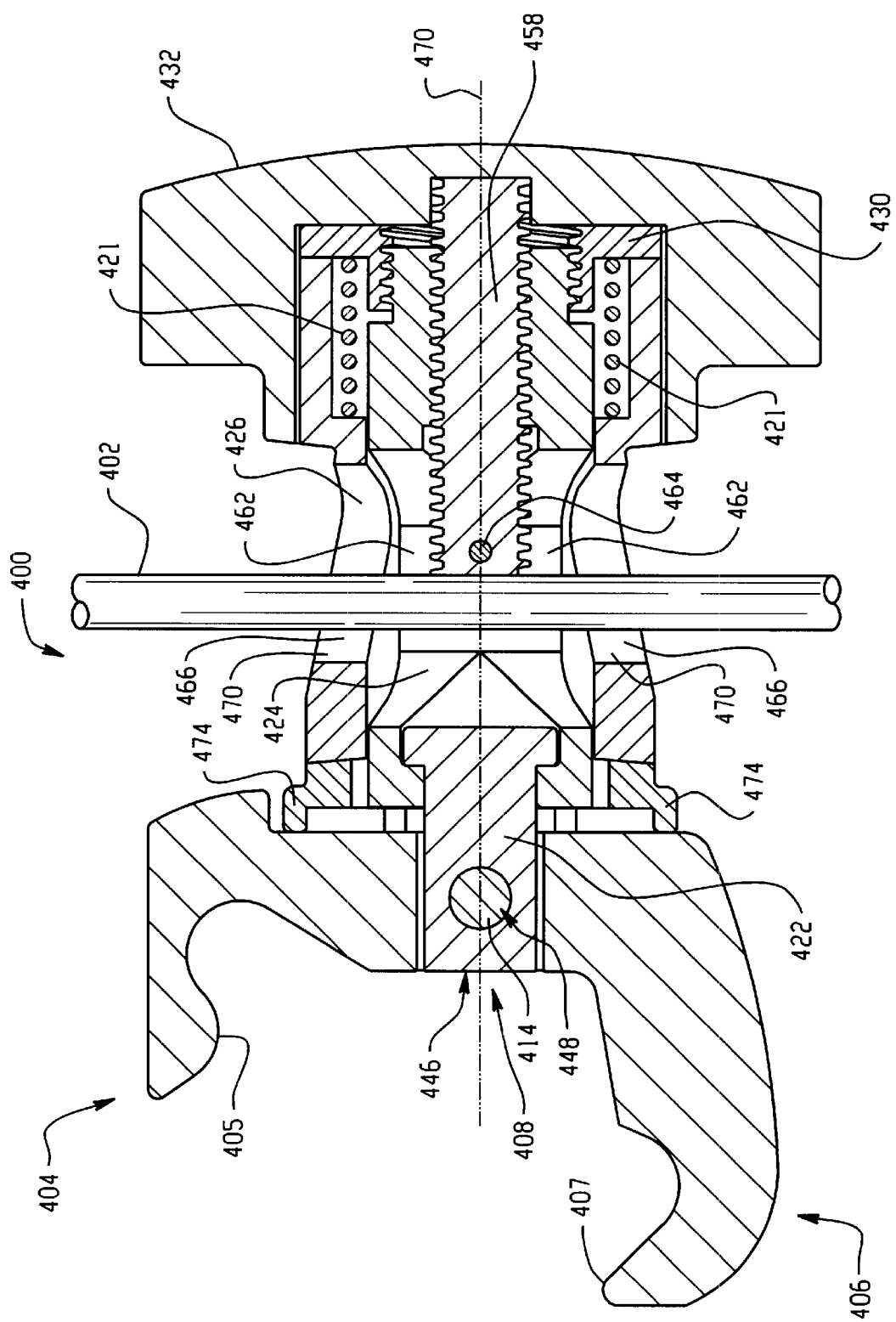

FIGS. 11a, 11b and 11c illustrate a dual jaw indirect clamp system 400 for attachment of a Clark socket accessory 401 and an associated post 402 to the surgical table described above in accordance with a fifth preferred embodiment of the invention. Associated post 402 is typically vertically oriented for holding an intravenous fluid source or the like. However, the overall Clark socket accessory permits the associated post to be positioned at essentially any non-vertically oriented angle.

The dual jaw indirect clamp system 400 includes an upper jaw member 404 which has a downwardly projecting lip 405 formed to conformably engage a section of the top recess or connection area 72 of the patient support member 60. Upper jaw member 404 is pivotally attached to a lower jaw member 406 which has a lower catch area or hook 407 formed to surroundingly engage a section of the flared lower edge 134 of the patient support member 60. Preferably, a hinge region 408 is formed at the connection interface between the upper and lower jaw members. In the embodiment illustrated, the upper jaw member 404 includes a pair of spaced apart hinge ears 410. The hinge ears are provided with holes 412 to receive a dowel pin 414. Dowel pin 414 extends through suitable openings provided on a second pair of hinge ears 416 arranged on the lower jaw member 406 opposite from the upper hinge area 410.

The clamping mechanism is a modified Clark socket including a gear plate 420, inner sleeve pin or insert 422, inner sleeve 424, outer sleeve 426, locking key 428, back washer 430, and threaded knob 432 with spring pin 434. The assembly is constructed by inserting inner sleeve pin 422 into the post hole opening 462 of inner sleeve 424 so that the narrow-diameter end 442 of inner sleeve pin 422 protrudes from second end 444 of inner sleeve 424. Inner sleeve pin 422 then passes through gear plate 420 and into the opening 446 defined by upper jaw member 404 and lower jaw member 406. An opening 448 in the narrow end 442 of inner sleeve pin 422 receives dowel pin 414 therethrough. Outer sleeve 426 receives inner sleeve 424 with locking key 428 therebetween, and a tooth ring 450 of outer sleeve 426 mates with a tooth ring 452 of gear plate 420. Back washer 430 threads onto outer threads 454 of inner sleeve 424 to loosely retain outer sleeve 426 thereon, whereby an assembly is formed which is connected to dowel pin 414 through inner sleeve pin 422. A spring 421 is captured between the back washer 430 and the outer sleeve 426 as shown. The spring biases the back washer 430 and outer sleeve into separation causing the jaws to be held in a normally closed or clamped relative position. The spring base is overcome by simple manual opening of the jaws. The threaded stub 458 of knob 432 is then inserted into the assembly and threaded through the inner threads of inner sleeve 424 until an end 460 protrudes into post hole 462 of inner sleeve 424. Spring pin 464 is then inserted into stub 458 to loosely retain the stub 458 in the assembly, whereby construction of dual jaw indirect clamp system 400 is completed.

In operation, an associated post 402 is inserted to extend completely through post hole 462 of inner sleeve 424 and post hole 466 which, as can be seen, are essentially coincident. Prior to post insertion, stub 458 must be withdrawn sufficiently using knob 432 to prevent stub tip 468 from blocking post 402. Spring pin 464 prevents the stub from being threaded completely out of inner threads 456 of inner sleeve 424 during the withdrawing. After post insertion, lip 405 of upper jaw member 404 is placed loosely on the top recess or connection area 72 of the patient support member 60, and hook 407 of lower jaw member 406 is positioned approximately to surroundingly engage a section of the flared lower edge 134 of the patient support member 60. In this loosened position, tooth ring 450 of outer sleeve 426 may be disengaged from tooth-ring 452 of gear plate 420, and the post may be rotated about axis 470 to obtain the desired post angle.

When the post is rotated to the desired position, knob 432 is then turned to tighten, whereby inner sleeve 424 is drawn toward knob 432. The drawing of inner sleeve 424 also draws connected inner sleeve pin 422 toward knob 432 whereby a force directed toward knob 432 is applied to dowel pin 414. Simultaneously, the turning of knob 432 acts to press tip 468 of stub 458 against associated post 402 which in turn presses against the "V"-shaped surfaces 472 of post hole 466 of outer sleeve 426. The force applied through associated post 402 presses outer sleeve 426 against gear plate 420 whereby tooth ring 450 of outer sleeve 426 re-engages with tooth ring 452 of gear plate 420, and gear plate 420 is pressed against upper jaw-member 404 and lower jaw member 406 at contacting bosses 474 of gear plate 420. The combination of the force on the dowel pin 414 with the force exerted by the contacting bosses 474 actuates the clamping action as upper jaw member 404 and lower jaw member 406 are drawn together about dowel pin 414. Removal of the dual jaw indirect clamp system 400 is effectuated simply by rotating knob 432 in the reverse direction whereby the above tightening points are loosened.

An advantage of clamp system 400 is that the tightening force is distributed across contacting bosses 474 of gear plate 420 and the corresponding contact surfaces of upper jaw member 404 and lower jaw member 406, as well as along the length of dowel pin 414. This large force distribution provides increased mechanical reliability and resistance to damage from overtightening and the like.

Figure 12A:
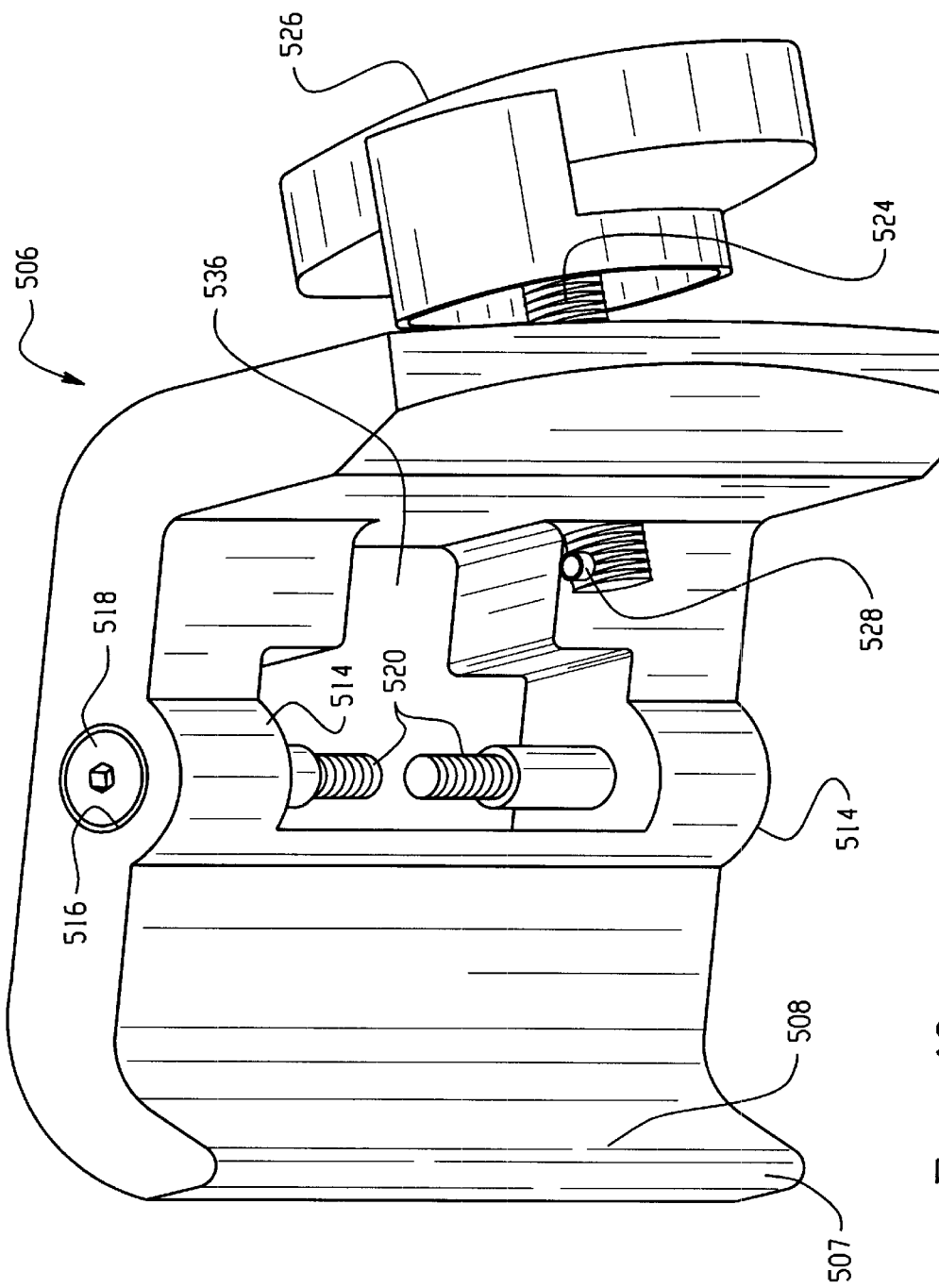
FIG. 12a is an isometric view showing a dual jaw indirect clamp system in a rail lock adaptor accessory in accordance with a sixth embodiment of the invention with the upper jaw member removed.
Figure 12B:
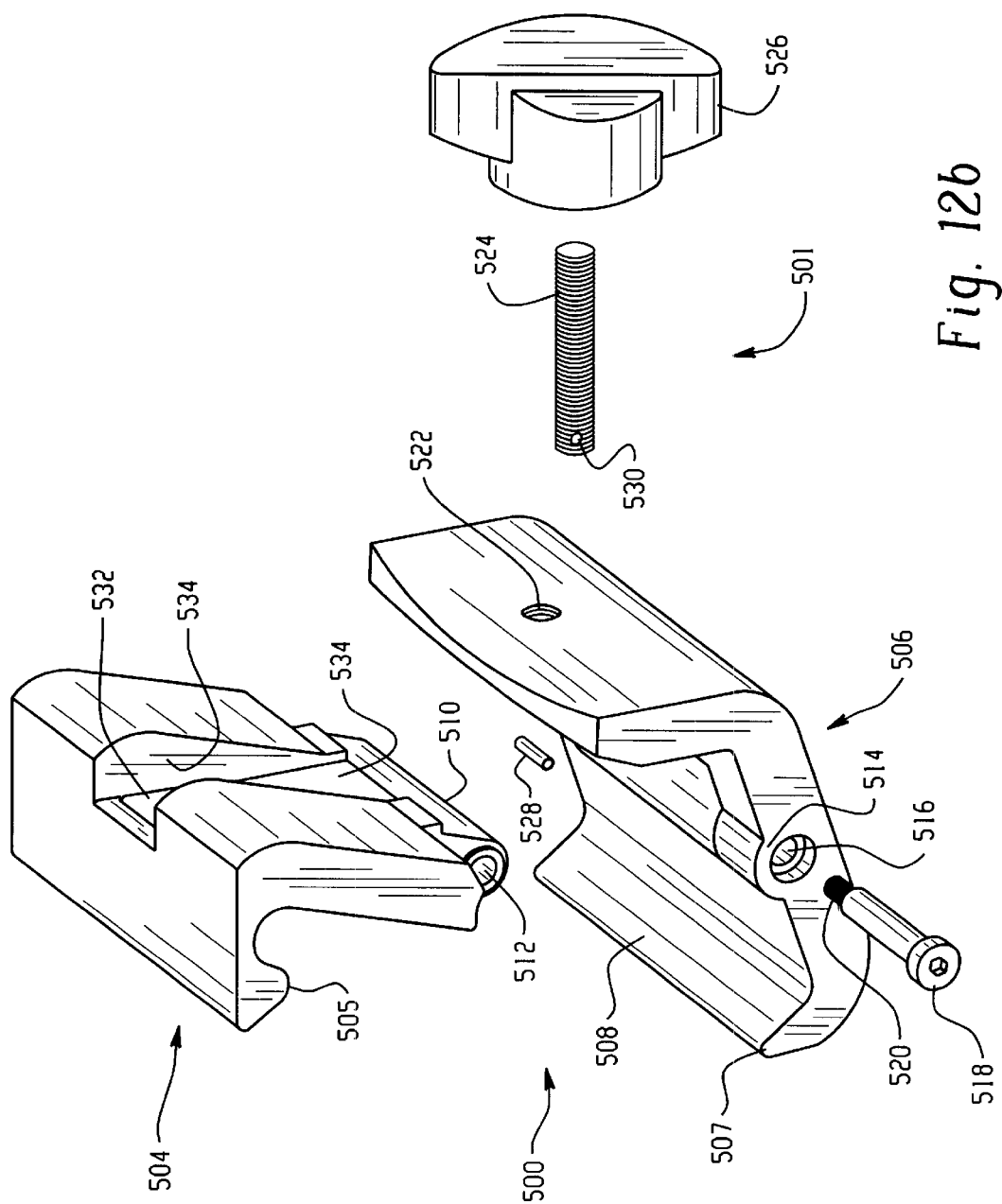
Figure 12C:
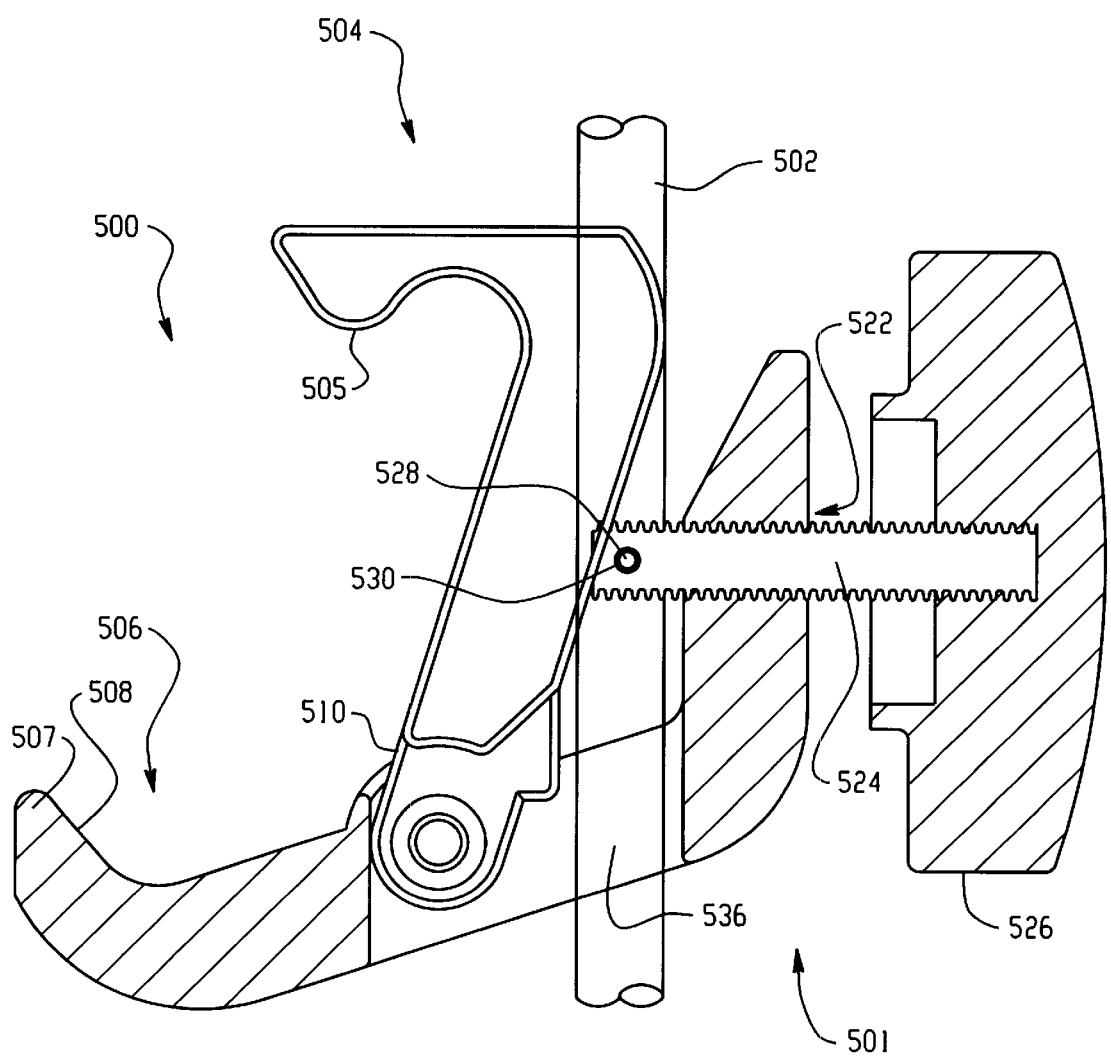
FIG. 12c is a cross-sectional view of the dual jaw indirect clamp system of FIGS. 12a and 12b.

FIGS. 12a, 12b and 12c illustrate a second dual jaw indirect clamp system 500 for attachment of a rail lock accessory 501 in accordance with a sixth, preferred embodiment of the invention. This clamp system is suitable for securing an associated flat-bar 502. Dual jaw indirect clamp system 500 includes an upper jaw member 504 which has a downwardly projecting lip 505 formed to conformably engage a section of the top recess or connection area 72 of the patient support member 60. Upper jaw member 504 is pivotally attached to a lower jaw member 506 which has a lower catch area or hook 507 formed to engage a section of the flared lower edge 134 of the patient support member 60. Upper jaw member 504 and lower jaw member 506 are pivotally attached in the following manner. Upper jaw member 504 includes a hinge ear 510 which has a threaded hole 512 passing therethrough. Lower jaw member 506 has two hinge ears 514 with unthreaded holes 516 passing therethrough. Two bolts 518 with threaded ends 520 form the pivot about which the hinge rotates. Each bolt inserts completely through the threaded hole 516 of a hinge ear 514 of lower jaw member 506 and thread partway into threaded hole 512 of hinge ear 510 of upper jaw member 504, so that lower jaw member 506 may pivot freely about the pivot formed by bolts 518 and threadedly secured into upper jaw member 504. Lower jaw member 506 has a threaded hole 522 which receives a threaded stud 524 which is in turn threadedly secured into a knob 526. Preferably, the securing of stud 524 to knob 526 is supplemented by an adhesive, thermal treatment, or the like. After insertion into threaded hole 522, a retaining pin 528 is inserted into hole 530 of stud 524 to prevent its inadvertent withdrawal.

Dual jaw indirect clamp system 500 operates as follows. Lip 505 of upper jaw member 504 is placed loosely on the top recess or connection area 72 of the patient support member 60. Hook 507 of lower jaw member 506 is positioned approximately to engage a section of the flared lower edge 134 of the patient support member 60. The associated flat-bar accessory 502 is inserted into a recess 532 defined by surfaces 534 of upper jaw and into an opening 536 in lower jaw member 506. Prior to tightening the clamp, flat-bar accessory 502 fits loosely and is slidably adjustable in the vertical direction, while the essentially conformable fit of the flat-bar 502 into recess 532 and opening 536 retains flat-bar 502 in an essentially vertical orientation. After the vertical position of the flat-bar is adjusted appropriately for the application, knob 526 is rotated to drive stud 524 against flat-bar 502 which in turn pushes against recess 532 of upper jaw member 504, whereby the clamping action is actuated as upper jaw member 504 and lower jaw member 506 are drawn together about pivot bolts 518. Removal of the dual jaw indirect clamp system 500 is effectuated simply by rotating knob 526 in the reverse direction whereby stud 524 is withdrawn and flat-bar 502 may be slidably removed from dual jaw indirect clamp system 500.

Figure 13A:
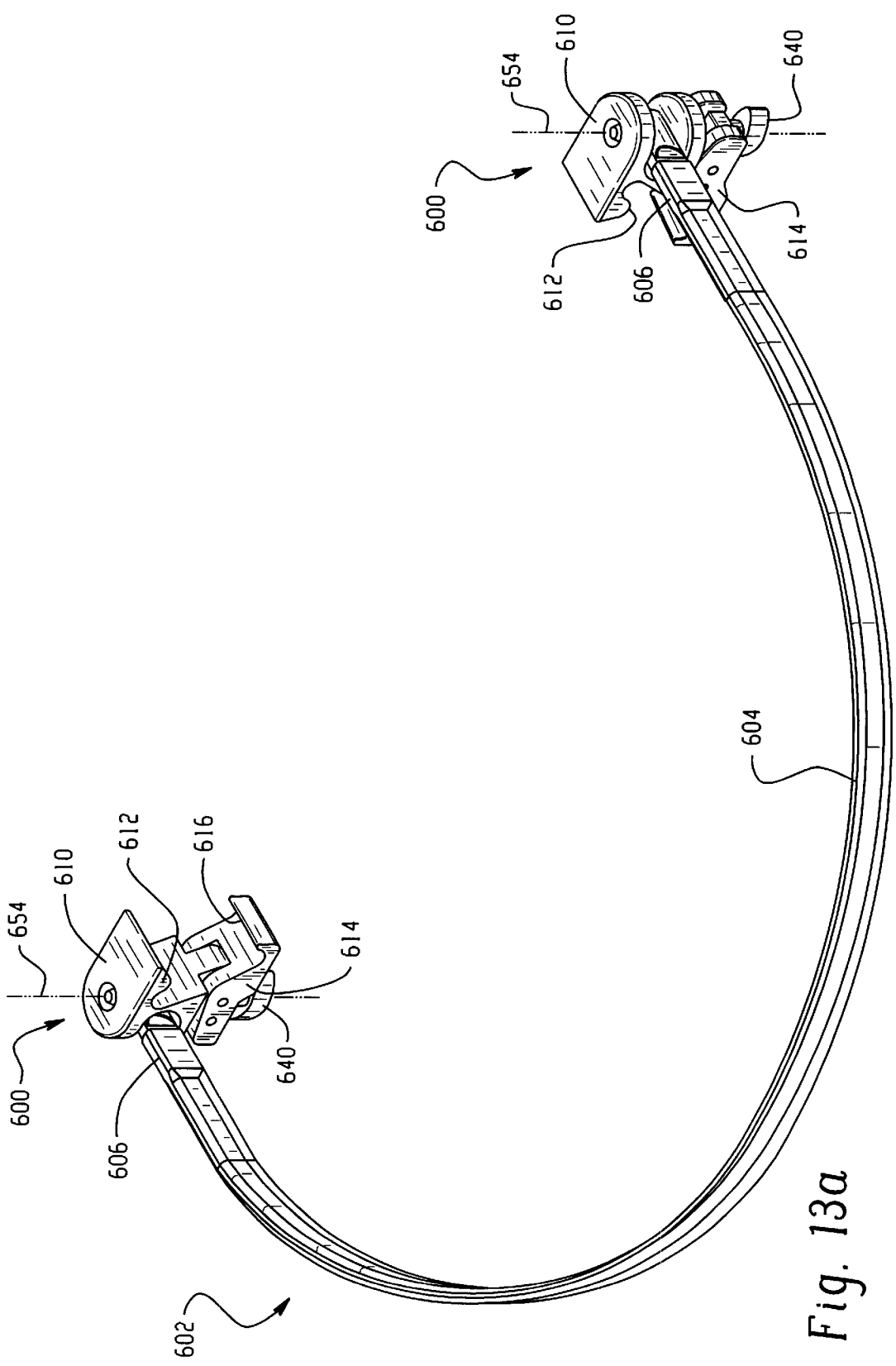
FIG. 13a is an isometric view showing a pair of pivot pin dual jaw direct clamp systems in a urological collector assembly in-accordance with a seventh embodiment of the invention.
Figure 13B:
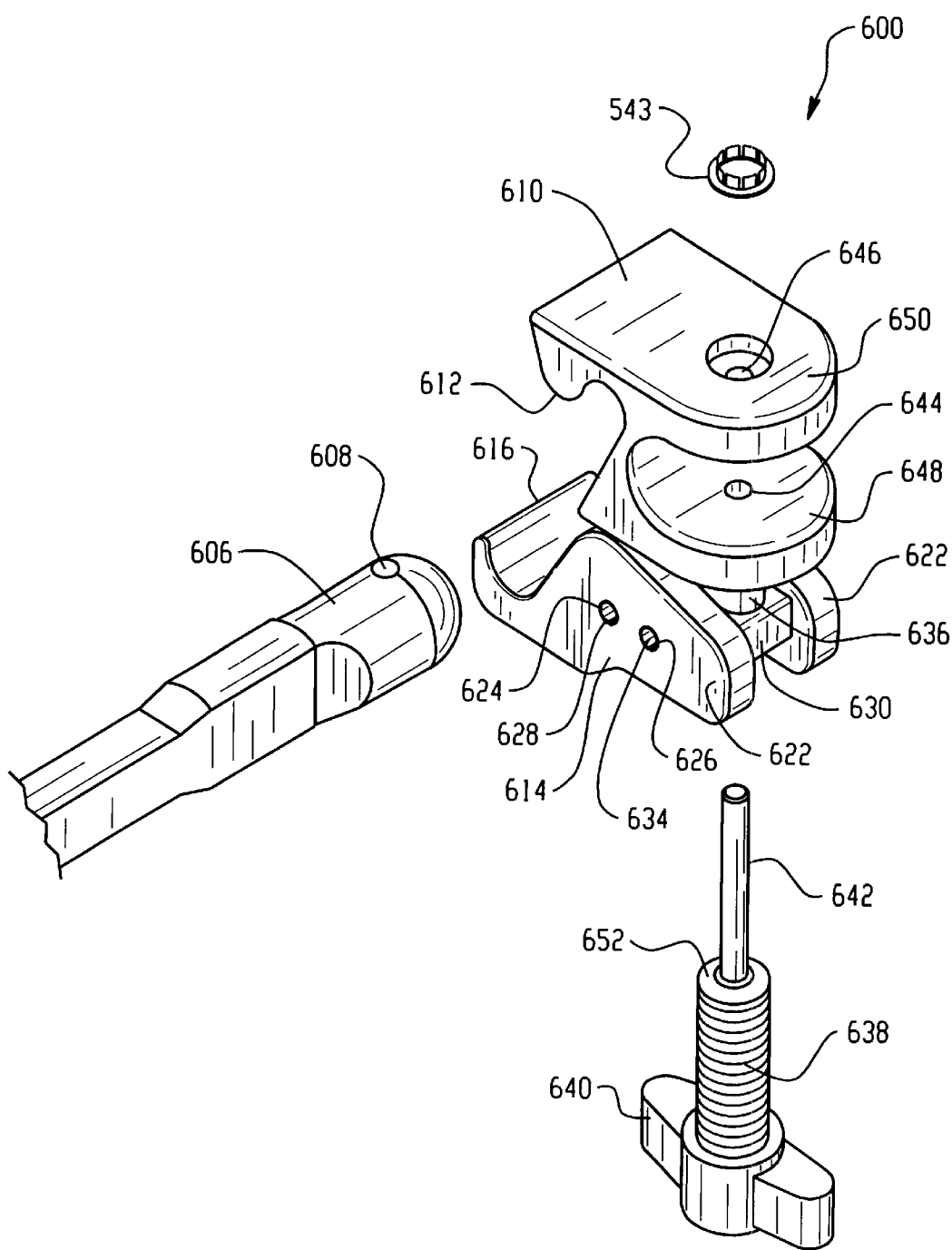
Figure 13C:
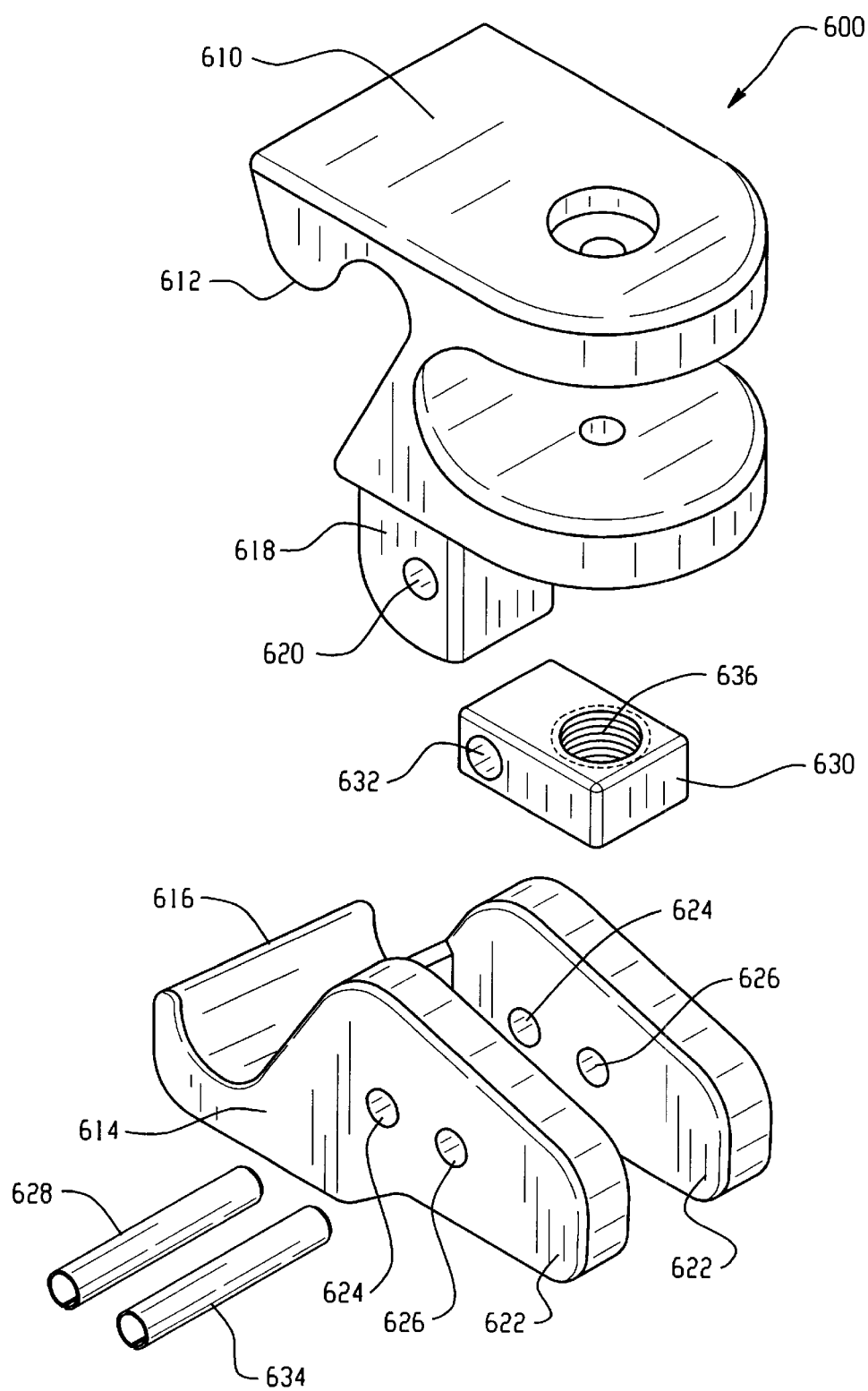
FIG. 13c is an exploded isometric view of the pivot pin clamp system of FIG. 13b; and, FIG. 13d is an isometric view showing an alternative pivot pin dual jaw direct clamp system in a urological collector assembly in accordance with an eighth embodiment of the invention.

FIGS. 13a, 13b and 13c illustrate a pair of pivot pin dual jaw direct clamp systems 600 for attachment of a urological collector accessory 602 to the table in accordance with a seventh preferred embodiment of the invention. In the illustrated embodiment, the urological collector accessory 602 includes a ring member 604 with ends 606 having holes 608 and an associated collection container (not shown) supported by ring member 604. In the preferred embodiment, ring member 604 is supported at both ends 606 by two clamp systems 600 as described next.

Clamp system 600 includes an upper jaw member 610 which has a downwardly projecting lip 612 formed to conformably engage a section of the top recess or connection area 72 of the patient support member 60. Upper jaw member 610 is pivotally attached to a lower jaw member 614 which has a lower catch area or hook 616 formed to surroundingly engage a section of the flared lower edge 134 of the patient support member 60. Upper jaw member 610 and lower jaw member 614 are pivotally attached in the following manner. Upper jaw member 610 includes a hinge ear 618 which has a hole 620 passing therethrough. Lower jaw member 614 has two large hinge ears 622 each having a first hole 624 passing therethrough, and each having a second hole 626 also passing therethrough. A first spring pin 628 passes through first holes 624 of the lower jaw member 614 and through hole 620 of hinge ear 618 of upper jaw member 610, whereby the pivotal attachment of upper jaw member 610 with lower jaw member 614 is obtained. A slider block 630 is positioned essentially between large hinge ears 622 of lower jaw member 614. Slider block 630 has a slotted hole 632 therein, and a second spring pin 634 passes through hole 632 as well as through second holes 626 of large hinge ears 622 of lower jaw member 614 whereby slider block 630 is pivotally attached to lower jaw member 614. Slider block 630 also has a threaded hole 636 passing therethrough and oriented perpendicularly to hole 632, which threadedly receives a threaded stud 638. Threaded stud 638 has a knob 640 attached to one end and has a post 642 parallel to stud 638 extending from the other end. As threaded stud 638 is threadedly engaged with threaded hole 636, post 642 passes through holes 644 and 646 in hemispherical extensions 648 and 650 extending from upper jaw member 610 and integral thereto. A star washer 643 is provided for connection onto the proximal end of the post 642 extending through the hole 646 in the upper extension 650. The star washer prevents the unintended removal of the post 642 from the lower jaw such as may be caused by loosening the knob 640 extremely. Snap rings or the like could be used for this purpose as well.

Clamp system 600 operates as follows. Lip 612 of upper jaw member 610 is placed loosely on the top recess or connection area 72 of the patient support member 60. Hook 616 of lower jaw member 614 is positioned approximately to surroundingly engage a section of the flared lower edge 134 of the patient support member 60. End 606 of associated urological collection assembly ring member 604 is inserted between hemispherical extensions 648 and 650 of upper jaw member 610. Hole 608 in end 606 of the associated ring member 604 is aligned with holes 644 and 646 of the hemispherical extensions 648, 650 and stud 638 with connected post extension 642 is inserted and threadedly attached using knob 640, whereupon post 642 passes through holes 644, 608, and 646 so that end 606 is pivotally attached to upper jaw member 610 about a pivot corresponding to post 642. As stud 638 threadedly progresses into hole 636 of slider block 630, stud end surface 652 presses against hemispherical extension 648 of the upper jaw member 610 whereby slider block 630 and hemispherical extension 648 are forced apart. This forcing apart effectuates the clamping action as upper jaw member 610 and lower jaw member 614 are urged together about pivot spring pin 628.

These operations are repeated using a second clamp system 600 at the other end 606 of ring member 604 to secure the ring member 604 to patient support member 60 at both ends. It is to be appreciated that end 606 is pivotally mounted, which allows pivotal flexibility about axis 654 which is parallel to hole 608 in end 606. This pivotal flexibility provides improved robustness by reducing the potential for dislodging or damaging urological collector assembly 602 by bumping and the like during routine surgical procedures.

Figure 13D:
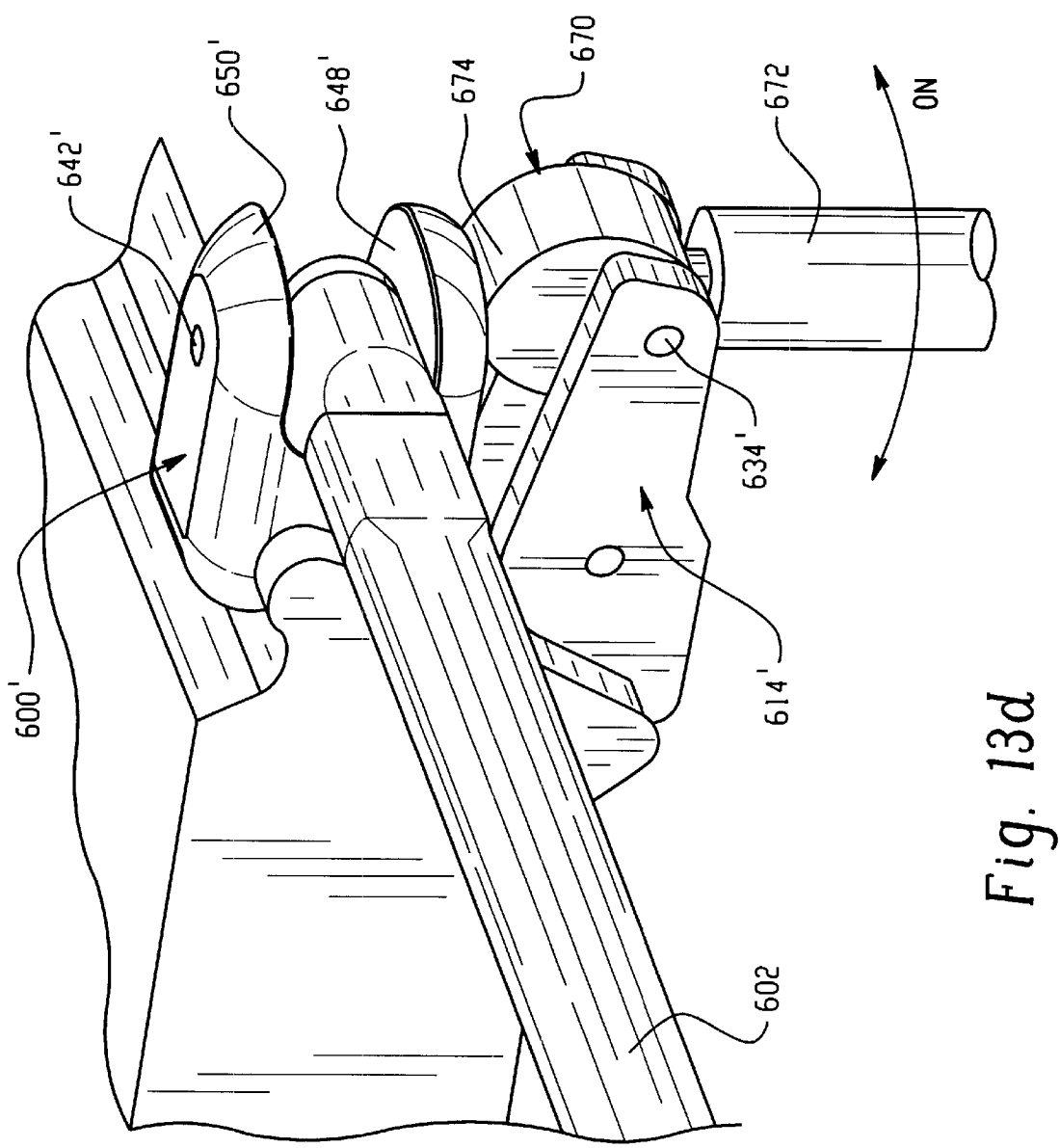

FIG. 13d illustrates a pivoting dual draw direct clamp system 600' for attachment of a urological collector accessory 602 to the table in accordance with an eight preferred embodiment of the invention. The clamp system 600' is essentially identical to the clamp system described above in connection with FIGS. 13a–13c with the exception of the clamping knob 640 and stud 638. A pin member 642' extends between the upper and lower hemispherical extensions 650', 648. A cam member 670 is attached to a lever arm 672 and is pivotable about the second spring pin 634'. Rotation of the clamping arm 672 in the direction marked ON urges the cam 670 into rotation about the pivot pin 634'. A high lobe 674 on the cam 670 urges the lower hemispherical member 648' away from the lower jaw member 614' to cause the clamping action described above.

In the illustrated embodiment, the cam and lever are directly connection for pivotal motion. Alternatively, in order to compensate for size variations in the associated surgical table edge interface profile, the cam can be spring mounted relative to the lower jaw member 614'.

The invention has been described with reference to the preferred embodiments. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. A clamping apparatus for securing an associated accessory to an outer edge of an associated patient support member, the outer edge having a top recess and a substantially planar side surface slanting inwardly from a top surface of the associated patient support table to a bottom surface of the associated patient support table and terminating in a flared lower edge extending beyond the bottom surface of the patient support member, the clamping apparatus comprising:

an upper jaw member having a downwardly projecting lip formed to essentially conformably engage a section of the top recess of the patient support member;

a lower jaw member having a hook region formed to surroundingly engage a section of the flared lower edge of the patient support member; and, a connection area joining the upper and lower jaw member including a direct connection between the upper and lower jaw members whereby the upper jaw member, the lower jaw member, and the direct connection form a single unitary piece made from a resilient material.

2. A clamping apparatus for securing an associated accessory to an outer edge of an associated patient support member, the outer edge having a top recess and an essentially planar side surface slanting inwardly from a top surface of the associated patient support table to a bottom surface of the associated patient support table and terminating in a flared lower edge extending beyond the bottom surface of the patient support member, the clamping apparatus comprising:

an upper jaw member having a downwardly projecting lip formed to conformably engage a section of the top recess of the patient support member;

a lower jaw member having a hook region formed to surroundingly engage a section of the flared lower edge of the patient support member;

a connection area joining the upper and lower jaw members, the connection including a direct connection between the upper and lower jaw members whereby the upper jaw member, the lower jaw member, and the direct connection form a single unitary piece made from a resilient material; and, a spring at least partially embedded in the upper jaw member whereby an associated accessory may be supported in a flexible manner by the clamping apparatus.

3. The clamping apparatus as set forth in claim 2, wherein:

the spring extends outside the unitary piece in an upward direction to provide a flexible hook for attaching the associated accessory.

4. A clamping apparatus for securing an associated accessory to an outer edge of an associated patient support member, the outer edge having a top recess and an essentially planar side surface slanting inwardly from a top surface of the associated patient support table to a bottom surface of the associated patient support table and terminating in a flared lower edge extending beyond the bottom surface of the patient support member, the clamping apparatus comprising:

an upper jaw member having a downwardly projecting lip formed to conformably engage a section of the top recess of the patient support member;

a lower jaw member having a hook region formed to surroundingly engage a section of the flared lower edge of the patient support member; and, a connection area joining the upper and lower jaw members including a hinge region with a pivot axis about which the upper and lower jaw members selectively relatively pivot and, a means for effectuating closure of the upper and lower jaw members whereby the clamping apparatus firmly clamps to a portion of the outer edge of the patient support member.

5. The clamping apparatus as set forth in claim 4, wherein the means for effectuating closure of the upper and lower jaw members comprises:

a Clark socket assembly adapted to simultaneously lock an associated post accessory to the associate patient support member.

6. A clamping apparatus for securing an associated accessory to an outer edge of an associated patient support member, the outer edge having a top recess and an essentially planar side surface slanting inwardly from a top surface of the associated patient support table to a bottom surface of the associated patient support table and terminating in a flared lower edge extending beyond the bottom surface of the patient support member, the clamping apparatus comprising:

an upper jaw member having a downwardly projecting lip formed to conformably engage a section of the top recess of the patient support member;

a lower jaw member having a hook region formed to surroundingly engage a section of the flared lower edge of the patient support member; and, a connection area joining the upper and lower jaw members, the connection area including:

a hinge region with a pivot axis about which the upper and lower jaw members selectively relatively pivot; and, means for effectuating closure of the upper and lower jaw members whereby the clamping apparatus firmly clamps to a portion of the outer edge of the patient support member, the means for effectuating closure including a central boss extending upwardly from the lower jaw member and having a pocket therein; and, a leaf spring member partially disposed in the central boss pocket and extending into a second pocket formed in the upper jaw member, whereby the closure is effectuated by a biasing spring force provided by the leaf spring member.

7. The clamping apparatus as set forth in claim 6, wherein the lower jaw member further comprises:

a boss extending from the lower jaw member and oriented such that a manual force applied to the boss counteracts said biasing spring force whereby the clamping apparatus is selectively manually removable from the associated patient support member outer edge.

8. The clamping apparatus as set forth in claim 6, wherein the upper jaw member further comprises:

an outwardly extending generally planar shelf member adapted to receive an associated armboard support platform accessory.

9. The clamping apparatus according to claim 6 further comprising:

a generally planar shelf member extending from the upper jaw member; and, a surgical armboard support platform.

10. The clamping apparatus according to claim 9 in combination with said patient support member.

11. The clamping apparatus according to claim 10 further comprising:

a plurality of rail standoffs; and, a plurality of features passing through holes in a surgical table rail member, through the rail standoffs, and into holes provided in the upper, jaw member.

12. The clamping apparatus according to claim 11 in combination with said patient support member.

13. The clamping apparatus as set forth in claim 6, wherein the upper jaw member further comprises:

a pair of spaced apart outwardly extending connection ears, each ear having an attachment opening;

a curved surface which together with the connection ears defines a curved recess; and, a connection pin extending between the ear attachment openings, the connection pin being adapted to hold a loop portion of an associated restraint strap.

14. The clamping apparatus according to claim 6 further comprising:

a pair of spaced apart connection ears extending from the upper jaw member, each ear defining an attachment opening;

a connection pin extending between the ear attachment openings; and, a restraint strap having a loop portion on an end, the loop surrounding the connection pin whereby the restraint strap is connected to the upper jaw.

15. The clamping apparatus according to claim 14 in combination with said patient support member.

16. A clamping apparatus for securing an associated accessory to an outer edge of an associated patient support member, the outer edge having a top recess and an essentially planar side surface slanting inwardly from a top surface of the associated patient support table to a bottom surface of the associated patient support table and terminating in a flared lower edge extending beyond the bottom surface of the patient support member, the clamping apparatus comprising:

an upper jaw member having a downwardly projecting lip formed to conformably engage a section of the top recess of the patient support member;

a lower jaw member having a hook region formed to surroundingly engage a section of the flared lower edge of the patient support member; and, a connection area joining the upper and lower jaw members, the connection area including a hinge region with a pivot axis about which the upper and lower jaw members selectively relatively pivot, the hinge region further including:

a dowel pin coincident with the pivot axis, a bottom hinge ear extending upwardly from the lower jaw member and having a hole therein adapted to receive the dowel pin, and, a top hinge ear extending downwardly from the upper jaw member and having a first hole therein adapted to receive the dowel pin, and further having a threaded hole therein which is perpendicularly oriented relative to the first hole; and, a means for effectuating closure of the upper and lower jaw members whereby the clamping apparatus firmly clamps to a portion of the outer edge of the patient support member, the means for effectuating closure of the upper and lower jaw members including: a push button, a knob, and a stud having one end affixed to the knob and having the other end passing through the push button and threaded into the threaded hole of the top hinge ear and selectively protruding therethrough whereby rotating the knob urges the stand into abutment against the push button which in turn abuts against the lower jaw member to cause relative motion between the upper and lower jaw members to thereby effectuate the closure.

17. The clamping apparatus as set forth in claim 16, further including:

a retaining pin inserted into a hole in the stud end protruding through the threaded hole of the top hinge ear whereby complete withdrawal of the stud from the threaded hole is prevented.

18. The clamping-apparatus as set forth in claim 16, further comprising:

a washer inserted over the stud between the push button and the threaded hole of the top hinge ear.

19. The clamping apparatus as set forth in claim 16, further comprising:

a washer inserted over the stud between the push button and the knob.

20. The clamping apparatus as set forth in claim 16, further comprising:

a plurality of rail standoffs; and, a plurality of fasteners passing through holes in an associated rail accessory and thence through the rail standoffs and fastening into receiving points of the upper jaw member, whereby the rail accessory is rigidly connected to the upper jaw member.

21. A clamping apparatus for securing an associated accessory to an outer edge of an associated patient support member, the outer edge having a top recess and an essentially planar side surface slanting inwardly from a top surface of the associated patient support table to a bottom surface of the associated patient support table and terminating in a flared lower edge extending beyond the bottom surface of the patient support member, the clamping apparatus comprising:

an upper jaw member having a downwardly projecting lip formed to conformably engage a section of the top recess of the patient support member;

a lower jaw member having a hook region formed to surroundingly engage a section of the flared lower edge of the patient support member;

a connection area joining the upper and lower jaw members, the connection area including a hinge region with a pivot axis about which the upper and lower jaw members selectively relatively pivot; and, means for effectuating closure of the upper and lower jaw members whereby the clamping apparatus firmly clamps to a portion of the outer edge of the patient support member, the means for effectuating including:

a Clark socket assembly adapted to simultaneously lock an associated post accessory to the associate patient support member, the Clark socket assembly including a gear plate having contacting bosses which contact the upper and lower jaw members over an extended area, and the hinge region including a dowel pin about which the hinge pivots.

22. The clamping apparatus according to claim 21 in combination with said patient support member.

23. A clamping apparatus for securing an associated accessory to an outer edge of an associated patient support member, the outer edge having a top recess and an essentially planar side surface slanting inwardly from a top surface of the associated patient support table to a bottom surface of the associated patient support table and terminating in a flared lower edge extending beyond the bottom surface of the patient support member, the clamping apparatus comprising:

an upper jaw member having a downwardly projecting lip formed to conformably engage a section of the top recess of the patient support member;

a lower jaw member having a hook region formed to surroundingly engage a section of the flared lower edge of the patient support member; and, a connection area joining the upper and lower jaw members, the connection area including a hinge region with a pivot axis about which the upper and lower jaw members selectively relatively pivot, and means for effectuating closure of the upper and lower jaw members whereby the clamping apparatus firmly clamps to a portion of the outer edge of the patient support member, the means for effectuating closure of the upper and lower jaw members including:

a knob; and, a stud, a first end of the stud being affixed to the knob and the second end being threaded into a threaded hole of the lower jaw member and protruding therethrough, whereby rotating the knob urges the stud into abutment with an associated flat bar accessory essentially conformably fitted within a recess of the upper jaw member and an opening in the lower jaw member to be pressed against the recess of the upper jaw member whereby the closure is effectuated.

24. The clamping apparatus as set forth in claim 23, further including:

a retaining pin inserted into a hole provided in the first end of the stud protruding through the threaded hole of the lower jaw member, the retaining pin preventing complete withdrawal of the stud from the threaded hole.

25. The clamping apparatus according to claim 23 in combination with said patient support member.

26. A clamping apparatus for securing an associated accessory to an outer edge of an associated patient support member, the outer edge having a top recess and an essentially planar side surface slanting inwardly from a top surface of the associated patient support table to a bottom surface of the associated patient support table and terminating in a flared lower edge extending beyond the bottom surface of the patient support member, the clamping apparatus comprising:

an upper jaw member having a downwardly projecting lip formed to conformably engage a section of the top recess of the patient support member;

a lower jaw member having a hook region formed to surroundingly engage a section of the flared lower edge of the patient support member; and, a connection area joining the upper and lower jaw members and a hinge region with a pivot axis about which the upper and lower jaw members selectively relatively pivot, the hinge region further including:

a first spring pin coincident with the pivot axis;

a second spring pin;

a slider block having a first hole for receiving the second spring pin, and having a threaded hole essentially perpendicularly oriented relative to the first hole;

a top hinge ear extending essentially downwardly from the upper jaw member and having a hole therein adapted to receive the first spring pin;

a pair of spaced apart extended bottom hinge ears extending essentially outwardly from the lower jaw member, each extended bottom hinge ear having a first hole adapted to receive the first spring pin whereby the upper and lower jaws are pivotally attached, and each extended bottom hinge ear having a second hole adapted to receive the second spring pin whereby the slider block is pivotally attached to the lower jaw member and pivotally held within the gap between the two spaced apart extended bottom hinge ears; and, means for effectuating closure of the upper and lower jaw members whereby the clamping apparatus firmly clamps to a portion of the outer edge of the patient support member, the means for effectuating closure of the upper and lower jaw members including:

a first extension of the upper jaw member extending over the pair of spaced apart extended bottom hinge ears and the slider block, the first extension having a hole therein that is substantially coaxially aligned with the threaded hole in the slider block, a second extension of the upper jaw member disposed above and substantially parallel relative to the first extension of the upper jaw member, the second extension having a hole therein that is substantially coaxially aligned with the hole in the first extension of the upper jaw member;

a knob; and, a stud, one end of which is rigidly affixed to the knob while the second end of which has a post extending therefrom essentially parallel to the stud axis, the stud being threaded into the threaded hole of the slider block, the post passing through the coaxial holes of the first and second extensions of the upper jaw member, whereby the closure is effectuated by transmission of the force of the second stud end against the first extension of the upper jaw member to the slider block and thence to the lower jaw member.

27. The clamping apparatus as set forth in claim 26, wherein:

the post extending from the second stud end passes through a hole in an end of a ring member of an associated urological collector assembly accessory whereby the ring member end is pivotally mounted between the first and second extensions of the upper jaw member.

28. The clamping apparatus according to claim 26 further comprising:

a urological collector assembly having a ring member provided with a hole on an end thereof, the post extending from the second stud end passing through said hole to pivotally fasten the urological collector to the clamping apparatus.

29. The clamping apparatus according to claim 28 in combination with the patient support member.

30. A clamping apparatus for use in securing an accessory to an outer edge of a patient support member, the outer edge having top and bottom surfaces and a substantially planar side surface slanting inwardly from the top surface to the bottom surface, the clamping apparatus comprising:

an upper jaw member shaped to conform with a portion of the top surface of the associated patient support member;

a lower jaw member shaped to conform with a portion of the lower surface of the associated patient support member; and, a connection area joining the upper and lower jaw members, the connection area including a direct connection between the upper and lower jaw members whereby the upper jaw member, the lower jaw member, and the direct connection form a single unitary piece made from a resilient material.

31. A clamping apparatus for use in securing an accessory to an outer edge of a patient support member, the outer edge having top and bottom surfaces and a substantially planar side surface slanting inwardly from the top surface to the bottom surface, the clamping apparatus comprising:

an upper jaw member shaped to conform with a portion of the top surface of the associated patient support member;

a lower jaw member shaped to conform with a portion of the lower surface of the associated patient support member; and, a connection area joining the upper and lower jaw members, the connection area including:

a hinge region with a pivot axis about which the upper and lower jaw members selectively relatively pivot; and, a means for effectuating closure of the upper and lower jaw members whereby the clamping apparatus firmly clamps to a portion of the outer edge of the associated patient support member.

32. The clamping apparatus according to claim 31, wherein the means for effectuating closure of the upper and lower jaw members includes:

a Clark socket assembly adapted to simultaneously lock an associated post accessory to the associate patient support member.

33. A clamping for use in securing an accessory to an outer edge of a patient support member, the outer edge having top and bottom surfaces and a substantially planar side surface slanting inwardly from the top surface to the bottom surface, the clamping apparatus comprising:

an upper jaw member shaped to conform with a portion of the top surface of the associated patient support member;

a lower jaw member shaped to conform with a portion of the lower surface of the associated patient support member; and, a connection area joining the upper and lower jaw members, and including a hinge region with a pivot axis about which the upper and lower jaw members selectively relatively pivot and means for effectuating closure of the upper and lower jaw members whereby the clamping apparatus firmly clamps to a portion of the outer edge of the associated patient support member, the means for effectuating closure of the upper and lower jaw members including:

a central boss extending upwardly from the lower jaw member and having a pocket therein; and, a leaf spring member partially disposed in the central boss pocket and extending into a second pocket formed in the upper jaw member, whereby the closure is effectuated by a biasing spring force provided by the leaf spring member.

34. A clamping apparatus for use in securing an accessory to an outer edge of a patient support member, the outer edge having top and bottom surfaces and a substantially planar side surface slanting inwardly from the top surface to the bottom surface, the clamping apparatus comprising:

an upper jaw member shaped to conform with a portion of the top surface of the associated patient support member;

a lower jaw member shaped to conform with a portion of the lower surface of the associated patient support member;

a connection area joining the upper and lower jaw members, the connection area including a hinge region with a pivot axis about which the upper and lower jaw members selectively relatively pivot, the hinge region further including:

a dowel pin coincident with the pivot axis, two bottom hinge ears extending essentially upward from the lower jaw member and having holes therein adapted to receive the dowel pin, and, a top hinge ear extending essentially downward from the upper jaw member and having a first hole therein adapted to receive the dowel pin, and further having a threaded hole therein which is essentially perpendicularly oriented relative to the first hole; and, means for effectuating closure of the upper and lower jaw members whereby the clamping apparatus firmly clamps to a portion of the outer edge of the associated patient support member, the means for effectuating closure of the upper and lower jaw members including:

a push button, a knob, and a stud having one end affixed to the knob and having the other end passing through the push button and threaded into the threaded hole of the top hinge ear and selectively protruding therethrough whereby rotating the knob urges the stand into abutment against the push button which in turn abuts against the lower jaw member to cause relative motion between the upper and lower jaw members to thereby effectuate the closure.

35. A clamping apparatus for use in securing an accessory to an outer edge of a patient support member, the outer edge having top and bottom surfaces and a substantially planar side surface slanting inwardly from the top surface to the bottom surface, the clamping apparatus comprising:

an upper jaw member shaped to conform with a portion of the top surface of the associated patient support member;

a lower jaw member shaped to conform with a portion of the lower surface of the associated patient support member; and, a connection area joining the upper and lower jaw members, the connection area including a hinge region with a pivot axis about which the upper and lower jaw members selectively relatively pivot, and means for effectuating closure of the upper and lower jaw members whereby the clamping apparatus firmly clamps to a portion of the outer edge of the associated patient support member, the means for effectuating closure of the upper and lower jaw members including:

a knob; and, a stud, a first end of the stud being affixed to the knob and the second end being threaded into a threaded hole of the lower jaw member and protruding therethrough in the general direction of the upper jaw member, whereby rotating the knob urges the stud into abutment with an associated flat bar accessory essentially conformably fitted within a recess of the upper jaw member and an opening in the lower jaw member to be pressed against the recess of the upper jaw member whereby the closure is effectuated.

36. A clamping apparatus for use in securing an accessory to an outer edge of a patient support member, the outer, edge having top and bottom surfaces and a substantially planar side surface slanting inwardly from the top surface to the bottom surface, the clamping apparatus comprising:

an upper jaw member shaped to conform with a portion of the top surface of the associated patient support member;

a lower jaw member shaped to conform with a portion of the lower surface of the associated patient support member; and, a connection area joining the upper and lower jaw members, the connection area including a hinge region with a pivot axis about which the upper and lower jaw members selectively relatively pivot, the hinge region further, including:

a first spring pin coincident with the pivot axis;

a second spring pin;

a slider block having a first hole for receiving the second spring pin, and having a threaded hole essentially perpendicularly oriented relative to the first hole;

a top hinge ear extending essentially downwardly from the upper jaw member and having a hole therein adapted to receive the first spring pin;

a pair of spaced apart extended bottom hinge ears extending essentially outwardly from the lower jaw member, each extended bottom hinge ear having a first hole adapted to receive the first spring pin whereby the upper and lower jaws are pivotally attached, and each extended bottom hinge ear having a second hole adapted to receive the second spring pin whereby the slider block is pivotally attached to the lower jaw member and pivotally held within the gap between the two spaced apart extended bottom hinge ears; and, means for effectuating closure of the upper and lower jaw members whereby the clamping apparatus firmly clamps to a portion of the outer edge of the associated patient support member, the means for effectuating closure of the upper and lower jaw members including:

a first extension of the upper jaw member extending over the pair of spaced apart extended bottom hinge ears and the slider block, the first extension having a hole therein that is substantially coaxially aligned with the threaded hole in the slider block, a second extension of the upper jaw member disposed above and substantially parallel relative to the first extension of the upper jaw member, the second extension having a hole therein that is substantially coaxially aligned with the hole in the first extension of the upper jaw member, a knob; and, a stud, one end of which is rigidly affixed to the knob while the second end of which has a post extending therefrom essentially parallel to the stud axis, the stud being threaded into the threaded hole of the slider block, the post passing through the coaxial holes of the first and second extensions of the upper jaw member, whereby the closure is effectuated by transmission of the force of the second stud end against the first extension of the upper jaw member to the slider block and thence to the lower jaw member.

* * * * *